United States Patent
Zhai et al.

(10) Patent No.: US 10,844,074 B2
(45) Date of Patent: *Nov. 24, 2020

(54) HETEROCYCLE COMPOUNDS AND USES THEREOF

(71) Applicant: ZHEJIANG JIANFENG-YIEN BIOTECHNOLOGY CO., LTD., Zhejiang (CN)

(72) Inventors: Haixiao Zhai, Bedford, MA (US); Fan Wu, Brookline, MA (US); Zhanggui Wu, Boston, MA (US)

(73) Assignee: ZHEJIANG JIANFENG-YIEN BIOTECHNOLOGY CO., LTD., Zhejiang (CN)

( * ) Notice: Subject to any disclaimer, the term of this patent is extended or adjusted under 35 U.S.C. 154(b) by 57 days.

This patent is subject to a terminal disclaimer.

(21) Appl. No.: 15/780,239

(22) PCT Filed: Dec. 2, 2016

(86) PCT No.: PCT/US2016/064507
§ 371 (c)(1),
(2) Date: May 31, 2018

(87) PCT Pub. No.: WO2017/096100
PCT Pub. Date: Jun. 8, 2017

(65) Prior Publication Data
US 2018/0346479 A1    Dec. 6, 2018

Related U.S. Application Data

(60) Provisional application No. 62/262,390, filed on Dec. 3, 2015.

(51) Int. Cl.
*C07D 495/04*    (2006.01)
(52) U.S. Cl.
CPC .................. *C07D 495/04* (2013.01)
(58) Field of Classification Search
None
See application file for complete search history.

(56) References Cited

U.S. PATENT DOCUMENTS

| | | |
|---|---|---|
| 6,503,914 B1 | 1/2003 | Benish et al. |
| 2010/0216789 A1 | 8/2010 | Nagarathnam et al. |
| 2015/0045324 A1 | 2/2015 | Cha et al. |
| 2015/0119379 A1 | 4/2015 | Butterworth et al. |

OTHER PUBLICATIONS

WO 2007/084815 A2 (Janssen Pharmaceutica, N.V.) Jul. 26, 2007 (Jul. 26, 2007); entire document.
PCT/US2016/064507 International Search Report.
PCT/US2016/064507 Written Opinion of the International Seaching Authority.
Elrazaz et al. "Thieno[2,3-d)pyrimidine based derivatives as kinase inhibitors and anticancer agents" Future Journal of Pharmaceutical Sciences. Sep. 25, 2015 (Sep. 25, 2015) vol. 1, p. 33-41; p. 35, left col., para 2 and 4.

*Primary Examiner* — Samantha L Shterengarts
(74) *Attorney, Agent, or Firm* — Duane Morris LLP; Thomas J. Kowalski; Deborah L. Lu

(57) ABSTRACT

Compounds having the general formula (I) and pharmaceutical compositions that can be used as Bruton's Tyrosine Kinase (BTK), ITK, JAK3, and selective mutant epidermal growth factor receptor tyrosine kinase (EGFR-TK) inhibitor and their uses in the treatment of related diseases and disorders such as cancer.

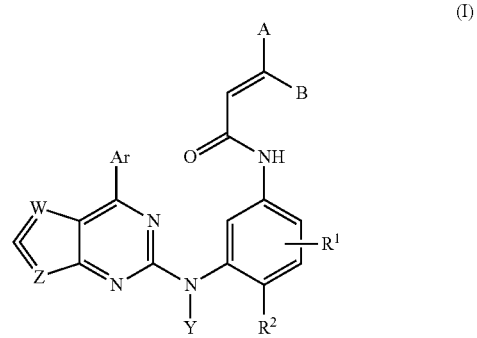

(I)

28 Claims, No Drawings

HETEROCYCLE COMPOUNDS AND USES THEREOF

FIELD OF THE INVENTION

The present invention relates to cancer treatment, specifically to compositions and methods of inhibiting the Bruton's tyrosine kinase (BTK) and other tyrosine kinases such as ITK, JAK3, and EGFR of cancer cells.

BACKGROUND OF THE INVENTION

BTK is a TEC family kinase. TEC family kinases consist of BTK, bone marrow tyrosine kinase on chromosome X (BMX), ITK (interleukin-2-inducible T-cell kinase), the Tec protein tyrosine kinase (TEC), and the TXK tyrosine kinase (TXK) that form the $2^{nd}$ largest family of non-receptor kinase in humans.

BTK contains an N-terminal Pleckstrin homology (PH) domain, a Tec homology (TH) domain, and Src homology (SH)-3, -2 and -1 (catalytic) domains (Smith Cie et al, BioEssays, 2001, 23, 436-46; Gomez-Rodriguez J et al, FEBS J, 2011, 278, 1980-9; Qi Q et al, FEBS J, 2011, 278, 1970-9)

Bruton's tyrosine kinase (BTK) is expressed in all hematopoietic cells and regulates B cell proliferation and survival. It's a key component of B cell receptor (BCR) signaling pathway and is a non-receptor protein tyrosine kinase. (Seda V et al, European Journal of Haematology, 2015, 94 (3), 193-205)

Tyrosine phosphorylation of BTK can be induced by stimulation of the B cell receptor (BCR). BTK is a key component of BCR signalling that regulates B cell proliferation and survival. Treatment with BTK inhibitors is expected to be more effective to B cell malignancies.

Overexpression of BTK increases tumor incidence and overall mortality (Kil, L. P. et al, Am. J. Blood Res., 2013, 3, 71-83; ter Brugge, P. J. et al, Blood, 2009, 114, 119-127). Aberrant activation of the BTK-dependent pathways has been implicated in maintaining malignant phenotype in a wide variety of malignancies. Dysregulating BTK activity can promote basal growth, survival, and cancer progression in mature B-cell lymphoproliferative disorders (Kuppers R, Nat Rev Cancer, 2005, 5(4), 251-262; Gururajan M et al, J Immunol, 2006, 176(10), 5715-5719; Buggy J J et al, Int Rev Immunol, 2012, 31(2), 119-132).

Inhibition of BTK interferes with multiple pathways that are potentially important for hematological cell survival, proliferation and migration in vivo.

Overexpression of epidermal growth factor receptor (EGFR) exists in about 70% of cancer patients (Seymour, L. K., Curr Drug Targets, 2001, 2, 117-133). EGFR tyrosine kinases are known therapeutic targets, and many products have been developed to inhibit their activities and block their signal transduction pathway, including FDA approved products such as Tarcevar, Irressa, and Gilotrif (all 4-amino-quinazoline-based inhibitors), all ATP-competitors. These agents have been widely used in EGFR-overexpressing as non-small cell lung cancer (NSCLC) patients including wild-type and activating mutation patients (W. Pao, Nat. Rev. Cancer, 2010, 10, 760-774; R. Rosell, Lancet Oncol, 2012, 13, 239-246; N. U. Lin, Breast Cancer Res, 2004, 6, 204-210).

There are two common activating mutations: L858R and delE746-A750. Mechanistic studies demonstrated that the clinical activity of Tarcevar and Iressa on activating mutant patients might be the results of the combined effects of enhanced inhibitor binding affinity to the mutant-kinase and addiction of mutant-cell to the oncogene (J A. Engelman, Science, 2007, 316, 1039-1043).

These so-called first- and second-generation inhibitors with 4-amino-quinazoline-based core structure, however, do not work well on about 50% of patients with relapsed and acquired resistant diseases, such as NSCLC. The acquired resistance is due to the mutation of gatekeeper residue of T790M (L V. Sequist, Sci Transl Med, 2011, 3, 75ra26; S. Kobayashi, N Engl J Med, 2005, 352, 786-792; W. Pao, PLoS Med, 2005, 2, 373; J A. Engelman, Semin Respir Crit Care Med, 2005, 26, 314-322). This mutation ($2^{nd}$ mutation) increases the ATP binding affinity to EGFR tyrosine kinase and affects the thermodynamic and kinetic binding characteristics of these inhibitors (C H. Yun, Proc Natl Acad Sci USA, 2008, 105, 2070-2075; Cancer Cell, 2007, 11, 217-227; M. Azam, Nat Struct Mol Biol, 2008, 15, 1109-1118; T A. Carter, Proc Natl Acad Sci USA, 2005, 102, 11011-11016). Further, the bulky methionine side chain in gatekeeper region prevents those drug molecules from the interaction with the ATP-binding pocket at clinically achievable concentrations.

The $2^{nd}$ generation covalent EGFR inhibitors, such as the FDA-approved Gilotrif and a compound under clinical trial, HKI-272, are effective on T790M mutant patients. Still, Gilotrif is limited to use in activating mutant patients because of its dose-limiting toxicities caused by the inhibition of wild-type EGFR.

Therefore there is a need for therapeutic agents which inhibit Bruton's Tyrosine Kinase, ITK, JAK3, and EGFR tyrosine kinases.

SUMMARY OF THE INVENTION

The present invention satisfies the above need and relates to fused pyrimidine derivatives which selectively and effectively inhibit cancers or tumors with Bruton's Tyrosine Kinase (BTK).

The compounds of the present invention are active on the therapeutic targets and are effective for treating diseases related to abnormal activity of Bruton's Tyrosine Kinase (BTK), ITK, JAK3, EGFR, and HER2, such as cancer.

The compounds of the present invention have the following general formula (I):

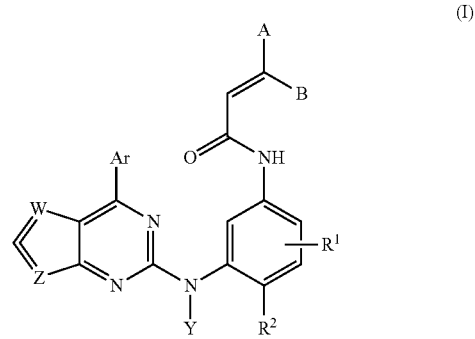

or a geometric isomer, a pharmaceutically acceptable salt, prodrug or solvate thereof, wherein Ar is aryl; substituted aryl; heteroaryl; substituted heteroaryl; heterocyclyl, cycloalkenyl, or cycloalkyl aryl; aryl fused heteroaryl; heteroaryl fused aryl; straight or branched, substituted or unsubstituted alkyl aryl or heteroaryl; substituted or unsubstituted alkenyl aryl or heteroaryl; substituted or unsubstituted alkynyl aryl or heteroaryl; arylakyl; arylalkenyl; arylalkynyl; heteroarylalkenyl; heteroarylalkenyl; or heteroarylalkynyl;
wherein one of W and Z is CH, and W is O, S, NH, $NR^3$ when Z is CH and Z is O, S, NH, $NR^3$ when W is CH,
A is H, C1-C6 alkyl, $-(CH_2)_nNR^4R^5$, wherein n=1-6;
B is H, C1-C6 alkyl, $-(CH_2)nN\ R^4R^5$, wherein n=1-6;
$R^1$ is H, halogen, SH, OH, $NO_2$, CN, $C_{1-6}$ alkyl, $C_{1-6}$ alkoxy, $C_{1-6}$ alkoxycarbonyl, $diC_{1-6}$ alkylamino$C_{2-6}$ alkylcarbonyl, amino, $C_{1-6}$ alkylamino, $diC_{1-6}$ alkylamino, carbamoyl, $C_{1-6}$ alkylcarbamoyl, di($C_{1-6}$ alkyl)carbamoyl, $diC_{1-6}$ alkylamino$C_{2-6}$ alkylcarbamoyl, sulfamoyl, $C_{1-6}$ alkylsulfonyl, $C_{1-6}$ alkylsulfinyl, $diC_{1-6}$ alkylamino$C_{2-6}$ alkylsulfamoyl, $diC_{1-6}$ alkylphsophonyl$C_{1-6}$ alkyl, hydroxy$C_{2-6}$ alkoxy, hydroxycarbonyl$C_{1-6}$ alkyl, $C_{1-6}$ alkoxy$C_{1-6}$ alkyl, $diC_{1-6}$ alkylamino$C_{2-6}$ alkylamino, substituted $diC_{1-6}$ alkylamino$C_{2-6}$ alkylamino, amino$C_{1-6}$ alkyl, $diC_{1-6}$ alkylaminoacetyl, hydroxydi$C_{2-6}$ alkylamino, $C_{1-6}$ alkylamino$C_{2-6}$ alkoxy, $diC_{1-6}$ alkylamino$C_{2-6}$ alkoxy, heteroaryl, heterocycle, heterocyclic oxy, heterocyclicthio, heterocyclicsulfinyl, heterocyclic sulfonyl, heterocyclic sulfamoyl, heterocyclic $C_{1-6}$ alkyl, heterocyclic $C_{1-6}$ alkoxy, heterocyclic amino, heterocyclic $C_{1-6}$ alkylamino, heterocyclic carbonyl, and heterocyclic $C_{1-6}$ alkylcarbonyl; wherein a heterocycle is saturated or partially unsaturated 3 to 8 membered cyclic or bicyclic hetero ring with one or more N, O, S, SO, and $SO_2$, in which C or the hetero atom may have one or more substituents selected from the group consisting of $C_{1-6}$ alkyl, hydroxy, hydroxy $C_{1-6}$ alkyl, $C_{1-6}$ alkylcarbonyl, $C_{1-6}$ alkyl amino, and di $C_{1-6}$ alkylamino;
$R^2$ is H, halogen, SH, OH, $NO_2$, CN, $C_{1-6}$ alkyl, $C_{1-6}$ alkoxy, $C_{1-6}$ alkoxycarbonyl, $diC_{1-6}$ alkylamino$C_{2-6}$ alkylcarbonyl, amino, $C_{1-6}$ alkylamino, $diC_{1-6}$ alkylamino, carbamoyl, $C_{1-6}$ alkylcarbamoyl, di($C_{1-6}$ alkyl)carbamoyl, $diC_{1-6}$ alkylamino$C_{2-6}$ alkylcarbamoyl, sulfamoyl, $C_{1-6}$ alkylsulfonyl, $C_{1-6}$ alkylsulfinyl, $diC_{1-6}$ alkylamino$C_{2-6}$ alkylsulfamoyl, $diC_{1-6}$ alkylphsophonyl$C_{1-6}$ alkyl, hydroxy$C_{2-6}$ alkoxy, hydroxycarbonyl$C_{1-6}$ alkyl, $C_{1-6}$ alkoxy$C_{1-6}$ alkyl, $diC_{1-6}$ alkylamino$C_{2-6}$ alkylamino, substituted $diC_{1-6}$ alkylamino$C_{2-6}$ alkylamino, amino$C_{1-6}$ alkyl, $diC_{1-6}$ alkylaminoacetyl, hydroxydi$C_{2-6}$ alkylamino, $C_{1-6}$ alkylamino$C_{2-6}$ alkoxy, $diC_{1-6}$ alkylamino$C_{2-6}$ alkoxy, heteroaryl, heterocycle, heterocyclic oxy, heterocyclicthio, heterocyclicsulfinyl, heterocyclic sulfonyl, heterocyclic sulfamoyl, heterocyclic $C_{1-6}$ alkyl, heterocyclic $C_{1-6}$ alkoxy, heterocyclic amino, heterocyclic $C_{1-6}$ alkylamino, heterocyclic carbonyl, heterocyclic $C_{1-6}$ alkylcarbonyl; wherein a heterocycle which is saturated or partially unsaturated 3 to 8 membered cyclic or bicyclic hetero ring with one or more N, O, S, SO, and $SO_2$, in which C or the hetero atom may has one or more substituents that consists of $C_{1-6}$ alkyl, hydroxy, hydroxy $C_{1-6}$ alkyl, $C_{1-6}$ alkylcarbonyl, $C_{1-6}$ alkyl amino, di $C_{1-6}$ alkylamino;
$R^3$ is $C_{1-6}$ alkyl, hydroxy $C_{1-6}$ alkyl, $C_{1-6}$ alkylamino $C_{2-6}$ alkyl, di $C_{1-6}$ alkylamino$C_{2-6}$ alkyl, $C_{1-6}$ alkylcarbonyl;
$R^4$ is H, $C_{1-6}$ alkyl, hydroxy $C_{1-6}$ alkyl, $C_{1-6}$ alkylamino $C_{2-6}$ alkyl, di $C_{1-6}$ alkyl, $C_{1-6}$ alkylcarbonyl;
$R^5$ is H, $C_{1-6}$ alkyl, hydroxy $C_{1-6}$ alkyl, $C_{1-6}$ alkylamino $C_{2-6}$ alkyl, di $C_{1-6}$ alkylamnino$C_{2-6}$ alkyl, $C_{1-6}$ alkylcarbonyl and Y is H, $C_{1-6}$ alkyl, aryl; substituted aryl; heteroaryl; substituted heteroaryl; heterocyclyl, cycloalkenyl, or cycloalkyl aryl.
Also provided are pharmaceutical compositions comprising the compounds of the present invention, and methods of treating cancers using the pharmaceutical compositions of the present invention.

In one embodiment, the compound of the present invention comprises Formula I wherein W is CH. In one embodiment, W is S.

In another embodiment, the compound of the present invention comprises Formula I wherein Z is CH. In one embodiment, Z is S.

In one embodiment, the compound of the present invention comprises Formula I (II):

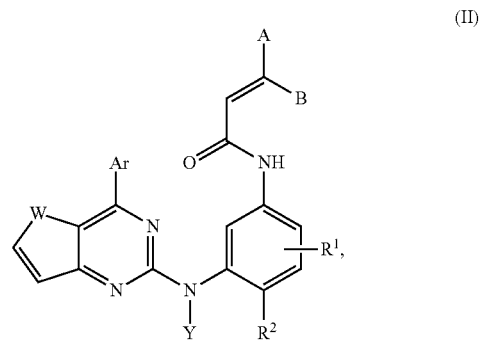

wherein $R^1$ is preferably selected from the group consisting of:

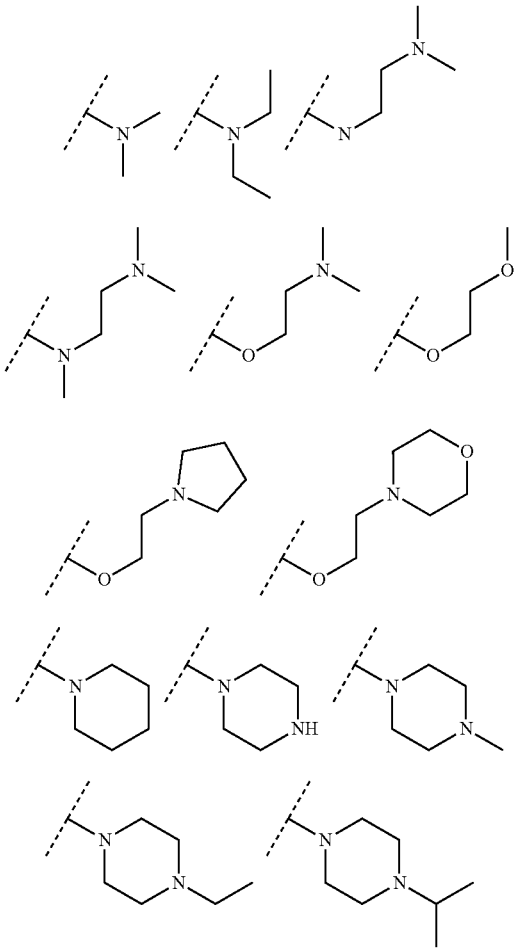

-continued
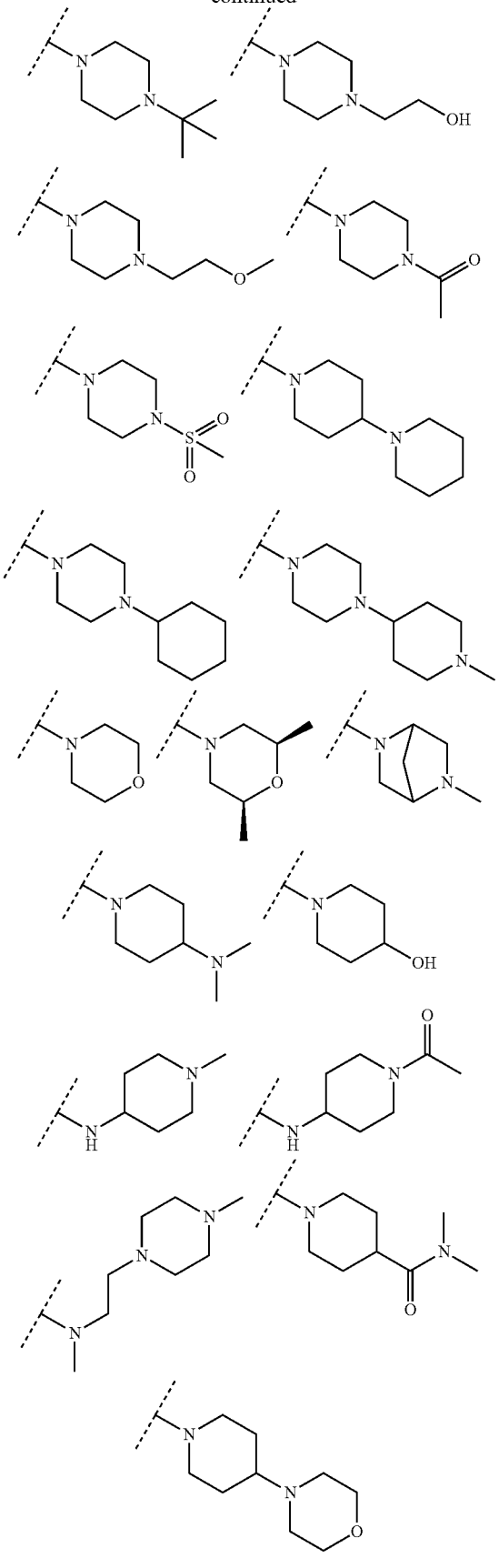
In one embodiment, the compound of the present invention comprises Formula I (III):
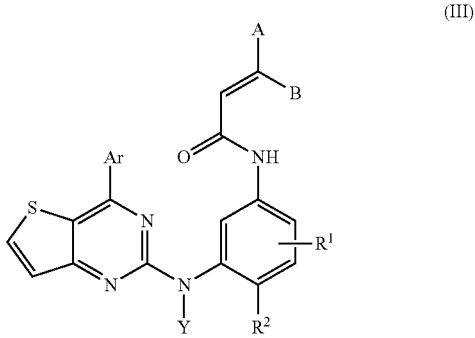
wherein $R^1$ is preferably selected from the group consisting:
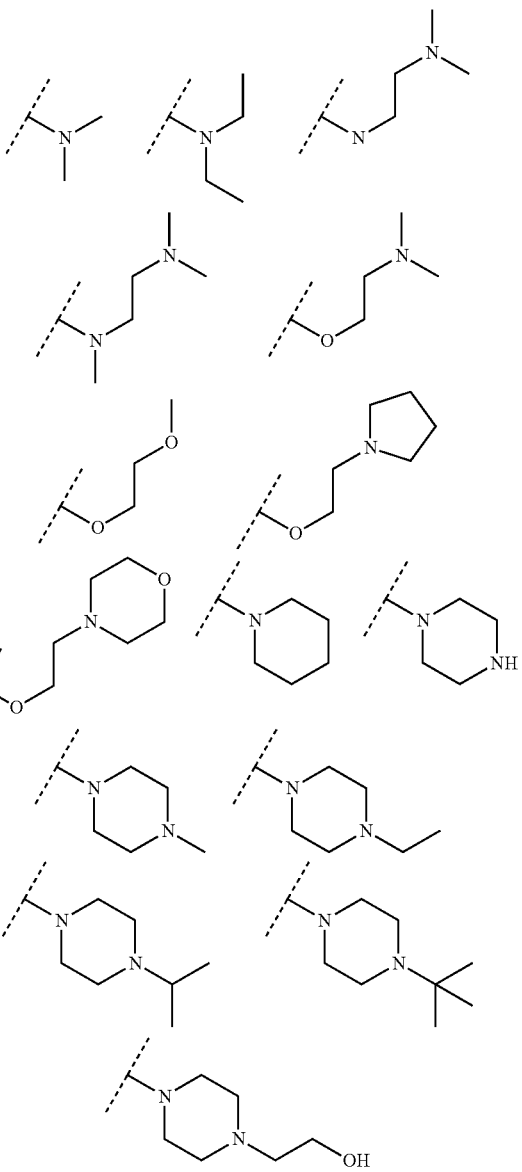

In one embodiment, the compound of the present invention comprises formula (IV):

$$\text{(IV)}$$

wherein R¹ is preferably selected from the group consisting:

-continued
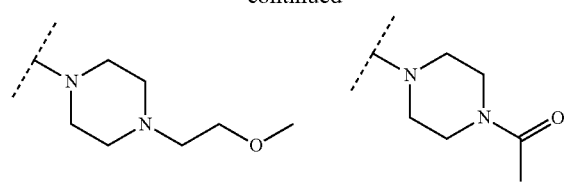
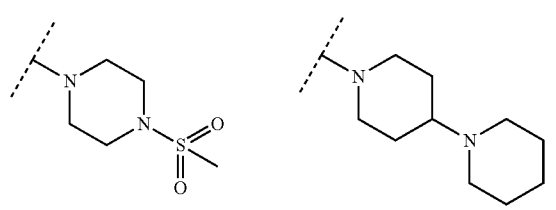
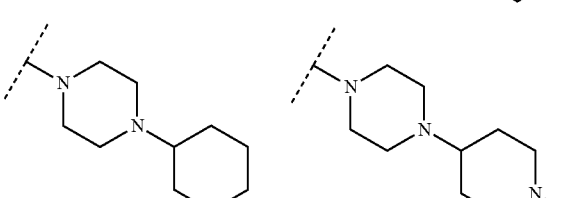
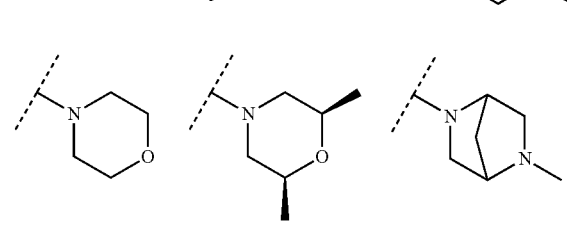
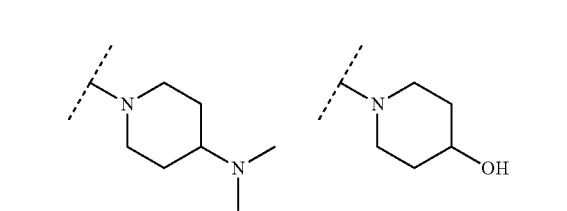
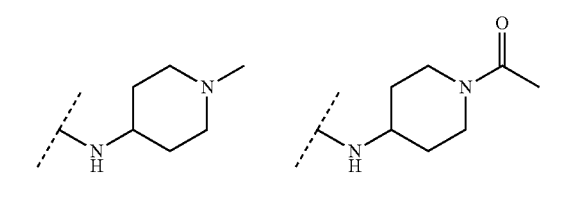
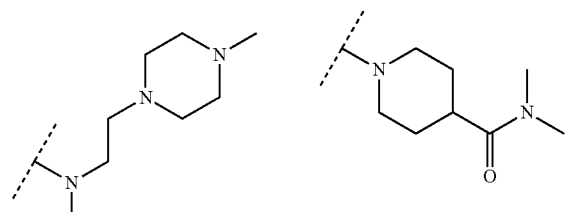
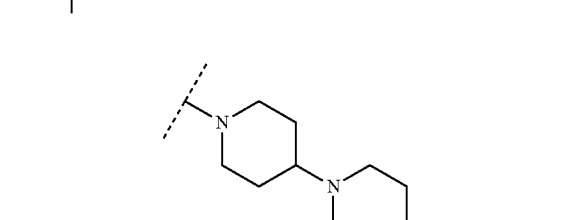
In one embodiment, the compound of the present invention comprises formula (V):
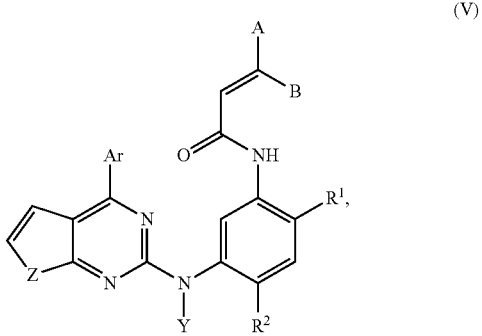
wherein $R^1$ is preferably selected from the group consisting:
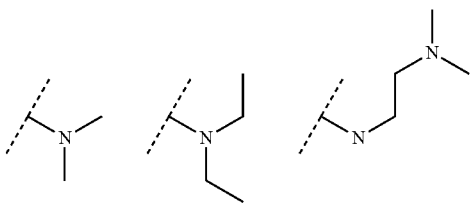
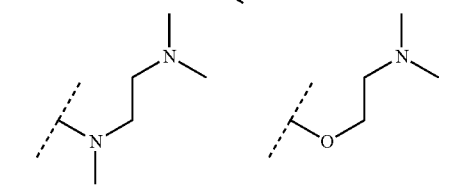
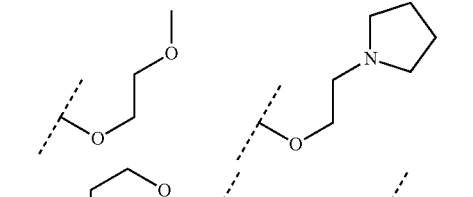
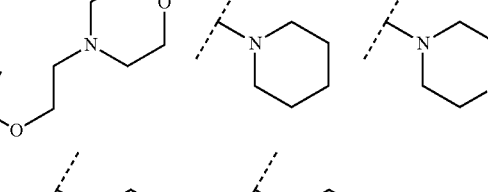
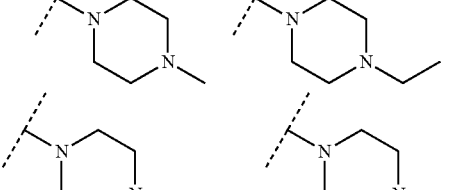
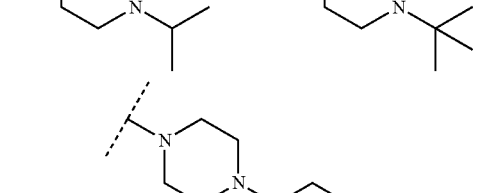

-continued
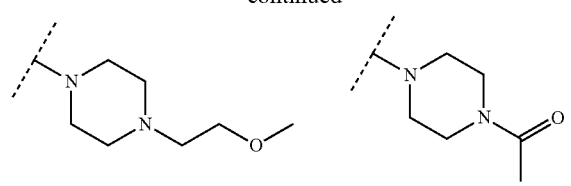
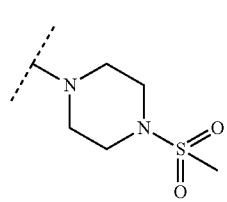
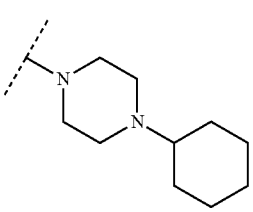
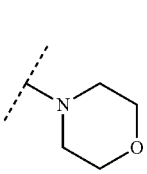
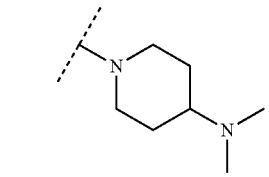
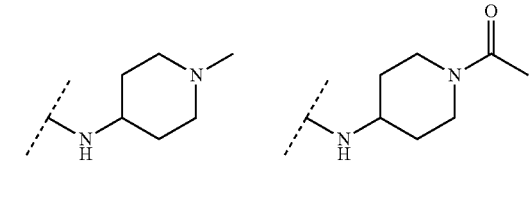
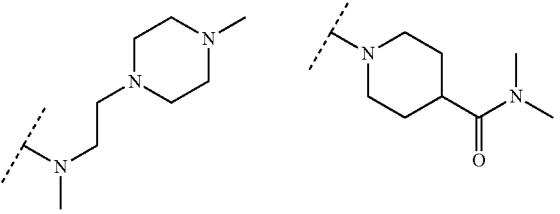
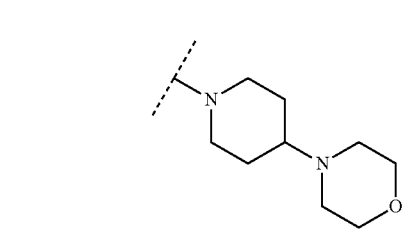
In one embodiment, the compound of the present invention comprises formula (VI):
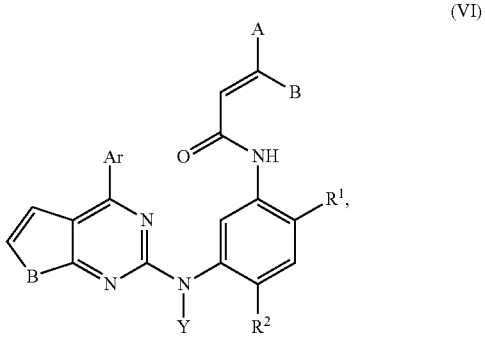
(VI)
wherein $R^1$ is preferably selected from the group consisting of:
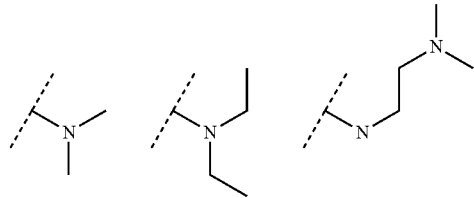
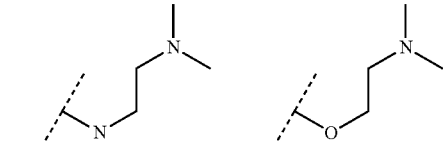
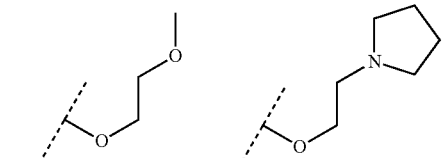
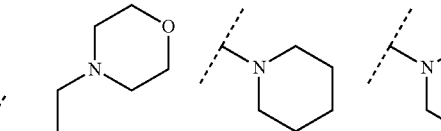
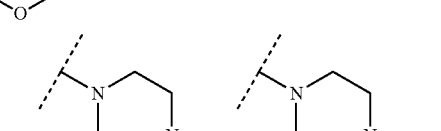
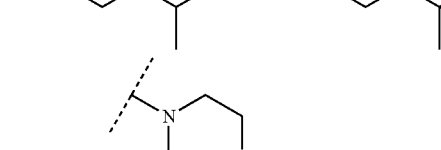

-continued

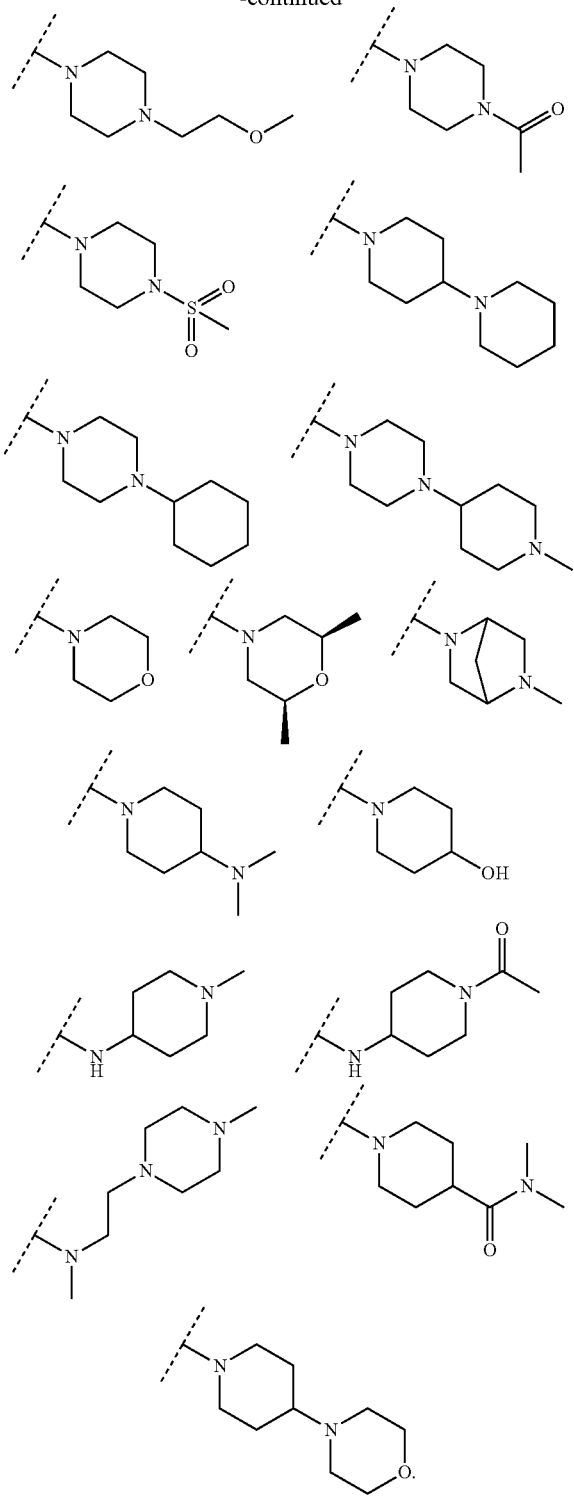

In specific embodiments the compound of the present invention are, selected from the group consisting of:
1: N-[2-[2-(dimethylamino)ethyl-methyl-amino]-5-[[4-(1H-indol-3-yl)thieno[3,2-d]pyrimidin-2-yl]amino]-4-methoxy-phenyl]prop-2-enamide,
2: N-[2-[4-(dimethylamino)-1-piperidyl]-5-[[4-(1H-indol-3-yl)thieno[3,2-d]pyrimidin-2-yl]amino]-4-methoxy-phenyl]prop-2-enamide,
3: N-[5-[[4-(1H-indol-3-yl)thieno[3,2-d]pyrimidin-2-yl]amino]-4-methoxy-2-[4-(methylamino)-1-piperidyl]phenyl]prop-2-enamide,
4: N-[2-(dimethylamino)-5-[[4-[3-(dimethylamino)phenyl]-4,4a-dihydrothieno[3,2-d]pyrimidin-2-yl]amino]-4-methoxy-phenyl]prop-2-enamide,
5: N-[5-[[4-[3-(tert-butylamino)phenyl]-4,4a-dihydrothieno[3,2-d]pyrimidin-2-yl]amino]-2-(dimethylamino)-4-methoxy-phenyl]prop-2-enamide,
6: N-[5-[[4-[3-(dimethylamino)phenyl]-4,4a-dihydrothieno[3,2-d]pyrimidin-2-yl]amino]-4-methoxy-2-(4-methyl-piperazin-1-yl)phenyl]prop-2-enamide,
7: N-[4-methoxy-5-[[4-[3-(methylamino)phenyl]-4,4a-dihydrothieno[3,2-d]pyrimidin-2-yl]amino]-2-(4-methylpiperazin-1-yl)phenyl]prop-2-enamide,
8: N-[5-[[4-[3-(dimethylamino)phenyl]-4,4a-dihydrothieno[3,2-d]pyrimidin-2-yl]amino]-4-methoxy-2-[methyl(2-morpholinoethyl)amino]phenyl]prop-2-enamide,
9: N-[4-methoxy-5-[[4-[3-(methylamino)phenyl]-4,4a-dihydrothieno[3,2-d]pyrimidin-2-yl]amino]-2-[methyl(2-morpholinoethyl)amino]phenyl]prop-2-enamide,
10: N-[5-[[4-[3-(dimethylamino)phenyl]-4,4a-dihydrothieno[3,2-d]pyrimidin-2-yl]amino]-4-methoxy-2-morpholino-phenyl]prop-2-enamide,
11: N-[5-[[4-[3-(tert-butylamino)phenyl]-4,4a-dihydrothieno[3,2-d]pyrimidin-2-yl]amino]-4-methoxy-2-morpholino-phenyl]prop-2-enamide,
12: N-[2-[2-(dimethylamino)ethoxy]-5-[[4-[3-(dimethylamino)phenyl]-4,4a-dihydrothieno[3,2-d]pyrimidin-2-yl]amino]-4-methoxy-phenyl]prop-2-enamide,
13: N-[2-[2-(dimethylamino)ethoxy]-4-methoxy-5-[[4-[3-(methylamino)phenyl]-4,4a-dihydrothieno[3,2-d]pyrimidin-2-yl]amino]phenyl]prop-2-enamide,
14: N-[5-[[4-[3-(dimethylamino)phenyl]-4,4a-dihydrothieno[3,2-d]pyrimidin-2-yl]amino]-4-methoxy-2-[2-(1-piperidyl)ethoxy]phenyl]prop-2-enamide,
15: N-[4-methoxy-5-[[4-[3-(methylamino)phenyl]-4,4a-dihydrothieno[3,2-d]pyrimidin-2-yl]amino]-2-[2-(1-piperidyl)ethoxy]phenyl]prop-2-enamide,
16: 1-[4-[[4-[3-(dimethylamino)phenyl]-4,4a-dihydrothieno[3,2-d]pyrimidin-2-yl]amino]-5-methoxy-2-(prop-2-enoylamino)phenyl]-N,N-dimethyl-piperidine-4-carboxamide,
17: 1-[5-methoxy-4-[[4-[3-(methylamino)phenyl]-4,4a-dihydrothieno[3,2-d]pyrimidin-2-yl]amino]-2-(prop-2-enoylamino)phenyl]-N,N-dimethyl-piperidine-4-carboxamide,
18: N-[4-methoxy-2-(4-methylpiperazin-1-yl)-5-[(4-phenyl-4,4a-dihydrothieno[3,2-d]pyrimidin-2-yl)amino]phenyl]prop-2-enamide,
19: N-[5-[[4-(3-aminophenyl)-4,4a-dihydrothieno[3,2-d]pyrimidin-2-yl]amino]-4-methoxy-2-(4-methylpiperazin-1-yl)phenyl]prop-2-enamide,
20: N-[2-[4-(dimethylamino)-1-piperidyl]-4-methoxy-5-[[4-(3-methoxyphenyl)-4,4a-dihydrothieno[3,2-d]pyrimidin-2-yl]amino]phenyl]prop-2-enamide,
21: N-[5-[[4-(1H-indol-3-yl)thieno[3,2-d]pyrimidin-2-yl]amino]-4-methoxy-2-(4-methylpiperazin-1-yl)phenyl]prop-2-enamide,
22: N-[4-methoxy-5-[[4-(1-methylindol-3-yl)thieno[3,2-d]pyrimidin-2-yl]amino]-2-(4-methylpiperazin-1-yl)phenyl]prop-2-enamide,
23: N-[5-[[4-(1H-indol-3-yl)thieno[3,2-d]pyrimidin-2-yl]amino]-4-methoxy-2-morpholino-phenyl]prop-2-enamide, 24: N-[5-[[4-[3-(dimethylamino)phenyl]thieno[3,2-d]pyrimidin-2-yl]amino]-4-methoxy-2-(4-methylpiperazin-1-yl)phenyl]prop-2-enamide,
25: N-[4-methoxy-5-[[4-[4-(methylamino)phenyl]thieno[3,2-d]pyrimidin-2-yl]amino]-2-(4-methylpiperazin-1-yl)phenyl]prop-2-enamide,
26: N-[4-methoxy-2-(4-methylpiperazin-1-yl)-5-[(4-phenylthieno[3,2-d]pyrimidin-2-yl)amino]phenyl]prop-2-enamide,
27: N-[5-[[4-[4-(tert-butylamino)phenyl]thieno[3,2-d]pyrimidin-2-yl]amino]-4-methoxy-2-(4-methylpiperazin-1-yl)phenyl]prop-2-enamide,
28: N-[2-[4-(dimethylamino)-1-piperidyl]-4-methoxy-5-[[4-(3-methoxyphenyl)-5-methyl-4,4a-dihydropyrrolo[3,2-d]pyrimidin-2-yl]amino]phenyl]prop-2-enamide,
29: N-[4-methoxy-5-[[4-[2-(methylamino)phenyl]thieno[3,2-d]pyrimidin-2-yl]amino]-2-(4-methylpiperazin-1-yl)phenyl]prop-2-enamide,
30: N-[4-methoxy-2-(4-methylpiperazin-1-yl)-5-[(4-phenylthieno[3,2-d]pyrimidin-2-yl)amino]phenyl]prop-2-enamide,
31: N-[2-[2-(dimethylamino)ethyl-methyl-amino]-4-methoxy-5-[[4-[2-(methylamino)phenyl]thieno[3,2-d]pyrimidin-2-yl]amino]phenyl]prop-2-enamide,
32: N-[2-[2-(dimethylamino)ethyl-methyl-amino]-4-methoxy-5-[(4-phenylthieno[2,3-d]pyrimidin-2-yl)amino]phenyl]prop-2-enamide,
33: N-[2-[2-(dimethylamino)ethyl-methyl-amino]-4-methoxy-5-[[4-[3-(methylamino)phenyl]thieno[2,3-d]pyrimidin-2-yl]amino]phenyl]prop-2-enamide,
34: N-[4-methoxy-5-[[4-(1-methylindol-3-yl)thieno[3,2-d]pyrimidin-2-yl]amino]-2-(2-morpholinoethoxy)phenyl]prop-2-enamide,
35: N-[4-methoxy-5-[[4-[3-(methylamino)phenyl]thieno[3,2-d]pyrimidin-2-yl]amino]-2-(2-morpholinoethoxy)phenyl]prop-2-enamide,
36: N-[4-methoxy-5-[[4-(1-methylindol-3-yl)thieno[3,2-d]pyrimidin-2-yl]amino]-2-morpholino-phenyl]prop-2-enamide,
37: N-[4-methoxy-5-[[4-[4-(methylamino)phenyl]thieno[3,2-d]pyrimidin-2-yl]amino]-2-morpholino-phenyl]prop-2-enamide,
38: N-[2-(dimethylamino)-4-methoxy-5-[[4-(1-methylindol-3-yl)thieno[3,2-d]pyrimidin-2-yl]amino]phenyl]prop-2-enamide,
39: N-[2-[ethyl(methyl)amino]-4-methoxy-5-[[4-[4-(methylamino)phenyl]thieno[3,2-d]pyrimidin-2-yl]amino]phenyl]prop-2-enamide,
40: N-[2-[ethyl(methyl)amino]-4-methoxy-5-[(4-phenylthieno[2,3-d]pyrimidin-2-yl)amino]phenyl]prop-2-enamide,
41: N-[2-[ethyl(methyl)amino]-4-methoxy-5-[[4-[3-(methylamino)phenyl]thieno[2,3-d]pyrimidin-2-yl]amino]phenyl]prop-2-enamide,
42: N-[4-methoxy-2-(4-methylpiperazin-1-yl)-5-[(4-phenylthieno[2,3-d]pyrimidin-2-yl)amino]phenyl]prop-2-enamide,
43: N-[4-methoxy-5-[[4-[2-(methylamino)phenyl]thieno[2,3-d]pyrimidin-2-yl]amino]-2-(4-methylpiperazin-1-yl)phenyl]prop-2-enamide,
44: N-[4-methoxy-5-[[4-(1-methylindol-7-yl)thieno[3,2-d]pyrimidin-2-yl]amino]-2-(4-methylpiperazin-1-yl)phenyl]prop-2-enamide,
45: N-[5-[[4-(1H-indol-7-yl)thieno[2,3-d]pyrimidin-2-yl]amino]-4-methoxy-2-(4-methylpiperazin-1-yl)phenyl]prop-2-enamide,
46: N-[4-methoxy-2-(4-methylpiperazin-1-yl)-5-[[4-(1-methylpyrrol-3-yl)thieno[2,3-d]pyrimidin-2-yl]amino]phenyl]prop-2-enamide,
47: N-[4-methoxy-2-(4-methylpiperazin-1-yl)-5-[[4-(1H-pyrrol-3-yl)thieno[2,3-d]pyrimidin-2-yl]amino]phenyl]prop-2-enamide,
48: N-[4-methoxy-2-(4-methylpiperazin-1-yl)-5-[[4-(1-methylpyrrol-3-yl)thieno[3,2-d]pyrimidin-2-yl]amino]phenyl]prop-2-enamide,
49: N-[4-methoxy-2-(4-methylpiperazin-1-yl)-5-[[4-(1H-pyrrol-3-yl)thieno[3,2-d]pyrimidin-2-yl]amino]phenyl]prop-2-enamide,
50: N-[5-[[4-[2-(dimethylamino)phenyl]thieno[2,3-d]pyrimidin-2-yl]amino]-4-methoxy-2-(4-methylpiperazin-1-yl)phenyl]prop-2-enamide,
51: N-[5-[[4-(1H-indol-3-yl)thieno[3,2-d]pyrimidin-2-yl]-methyl-amino]-4-methoxy-2-morpholino-phenyl]prop-2-enamide,
52: N-[4-methoxy-5-[methyl-[4-(1-methylindol-3-yl)thieno[3,2-d]pyrimidin-2-yl]amino]-2-morpholino-phenyl]prop-2-enamide,
53: N-[2-[2-(dimethylamino)ethyl-methyl-amino]-5-[[4-(1H-indol-3-yl)thieno[3,2-d]pyrimidin-2-yl]-methyl-amino]-4-methoxy-phenyl]prop-2-enamide, and
54: N-[2-[2-(dimethylamino)ethyl-methyl-amino]-4-methoxy-5-[methyl-[4-(1-methylindol-3-yl)thieno[3,2-d]pyrimidin-2-yl]amino]phenyl]prop-2-enamide A pharmaceutical composition of the present invention can be used for inhibiting the growth of a cancer cell which overexpresses the Bruton's Tyrosine Kinase (BTK) and other tyrosine kinases including ITK, JAK3, and EGFR tyrosine kinase, comprising administering an effective amount of a compound of claim 1 to the cell.

The present invention further provides for a method for treating a subject in need thereof, comprising administering to the subject a pharmaceutical composition of the present invention. In one embodiment, the subject is a human suffering from a diseased caused by abnormal cell proliferation, e.g. those caused by overexpression of BTK.

DETAILED DESCRIPTION OF THE INVENTION

The present invention provides fused pyrimidine derivatives which selectively and effectively inhibit cancers or tumors. The compounds of the present invention are active on the therapeutic targets and are effective in inhibiting Bruton's tyrosine kinase, ITK, JAK3, EGFR, and HER2 activities.

In a first embodiment, the compound has a structure of formula (I) illustrated below, or is its geometric isomers, enantiomers, diastereomers, racemates, pharmaceutically acceptable salts, prodrugs and solvates thereof:

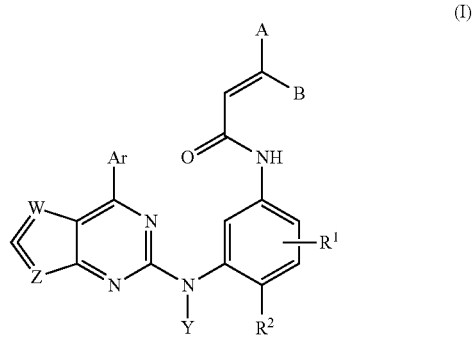

wherein A, B, Ar, $R^1$, $R^2$, W, Y, Z are as previous defined.

In a second embodiment, the compound has the formula (II) illustrated below, or its geometric isomers, enantiomers, diastereomers, racemates, pharmaceutically acceptable salts, prodrugs and solvates thereof:

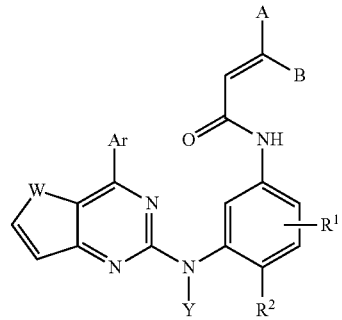

(II)

wherein W is O, S, NH, $NR^3$; and A, B, Ar, Y, $R^1$, $R^2$, $R^3$, are as previous defined. Examples of $R^1$ include substituents selected from but are not limited to the groups of the following formulae:

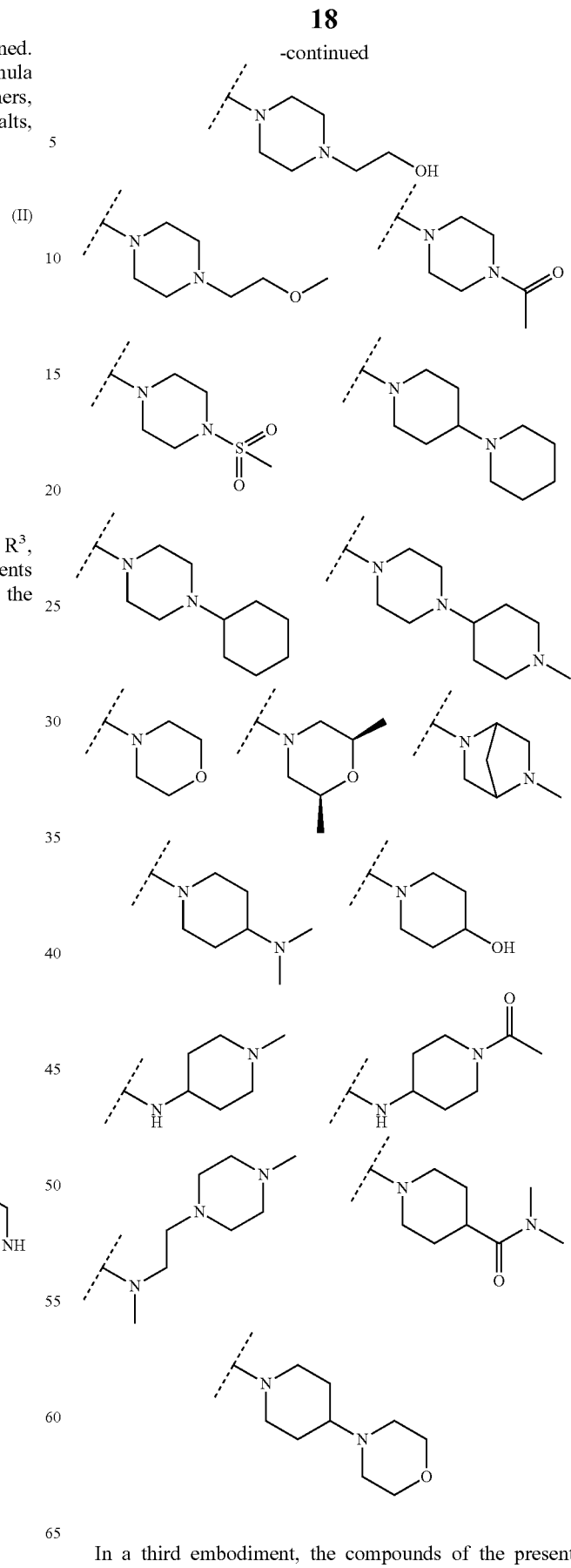

In a third embodiment, the compounds of the present invention has Formula (III) illustrated below, or its geometric isomers, enantiomers, diastereomers, racemates, pharmaceutically acceptable salts, prodrugs and solvates thereof:

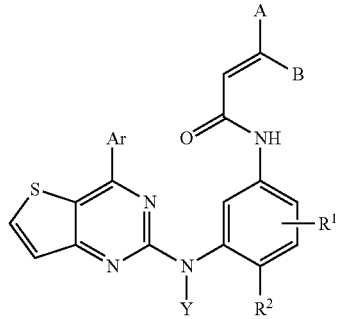

(III)

wherein A, B, Ar, Y, $R^1$, $R^2$ are as previous defined. Examples of $R^1$ include substituents selected from but are not limited to the group of the following formulae:

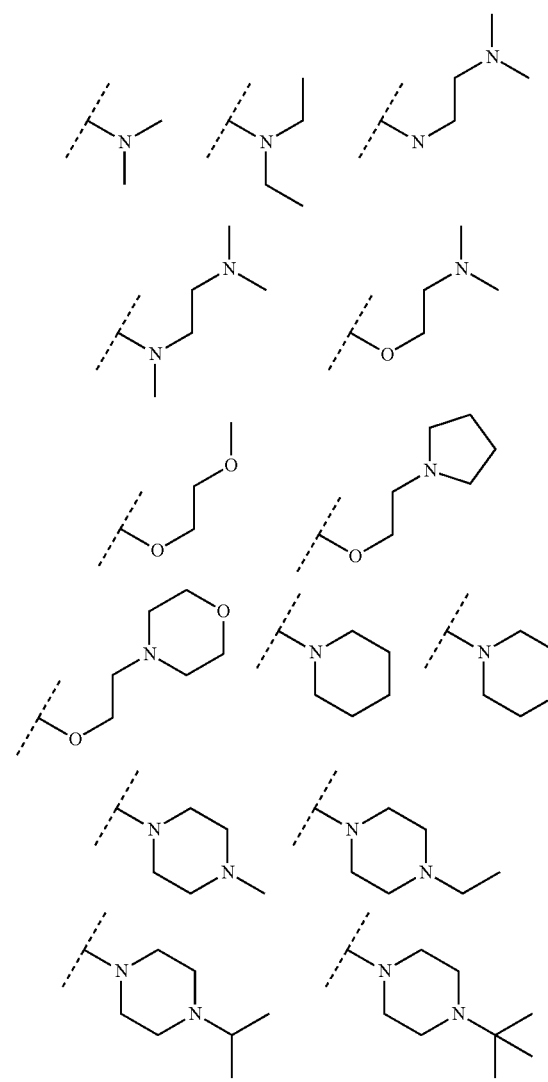

-continued

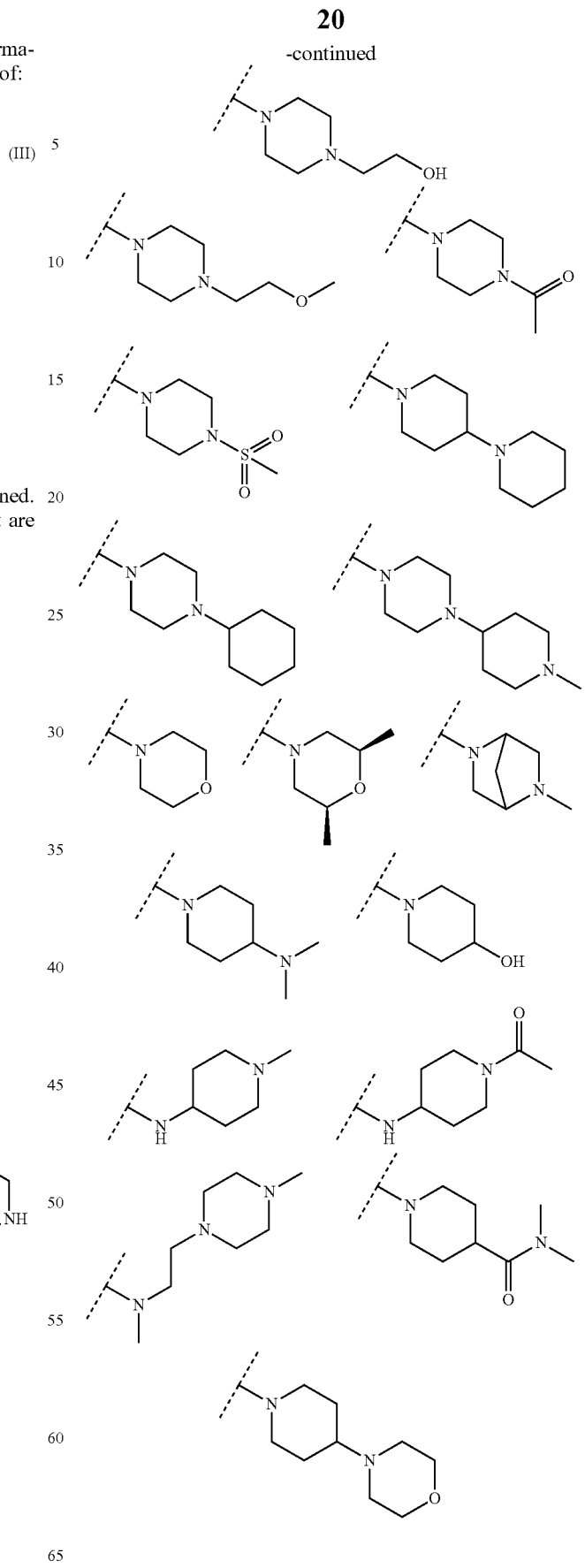

In a fourth embodiment, the compound has the formula (IV) illustrated below, or its geometric isomers, enantiomers, diastereomers, racemates, pharmaceutically acceptable salts, prodrugs and solvates thereof:
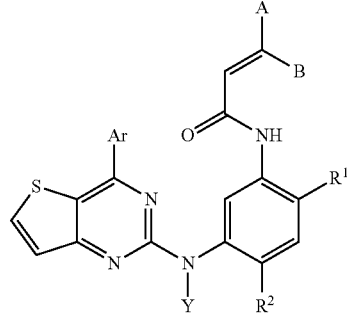
(IV)
wherein A, B, Ar, Y, $R^1$, $R^2$ are as previous defined; examples of $R^1$ include substituents of the following formulae:
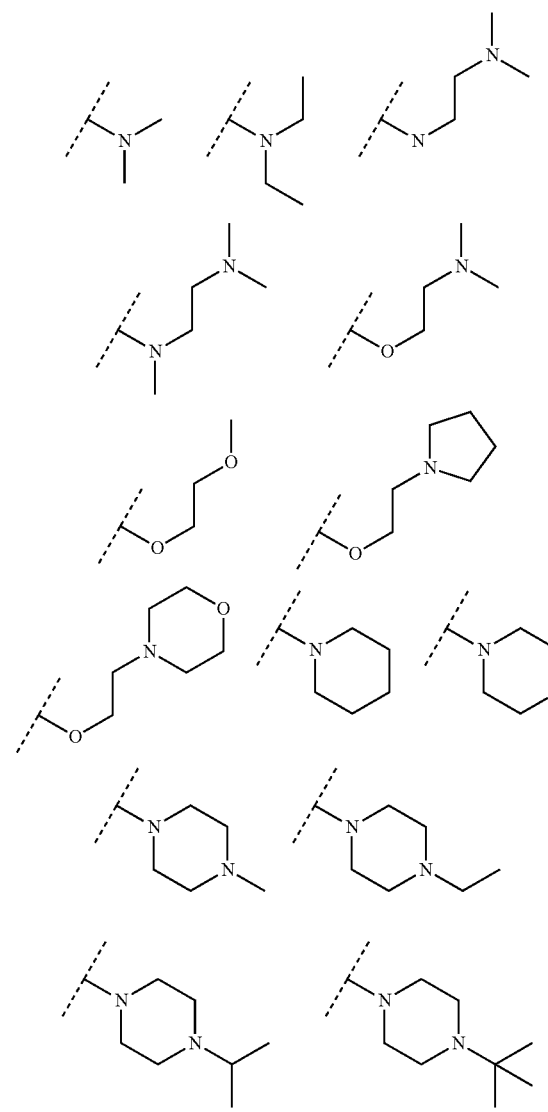
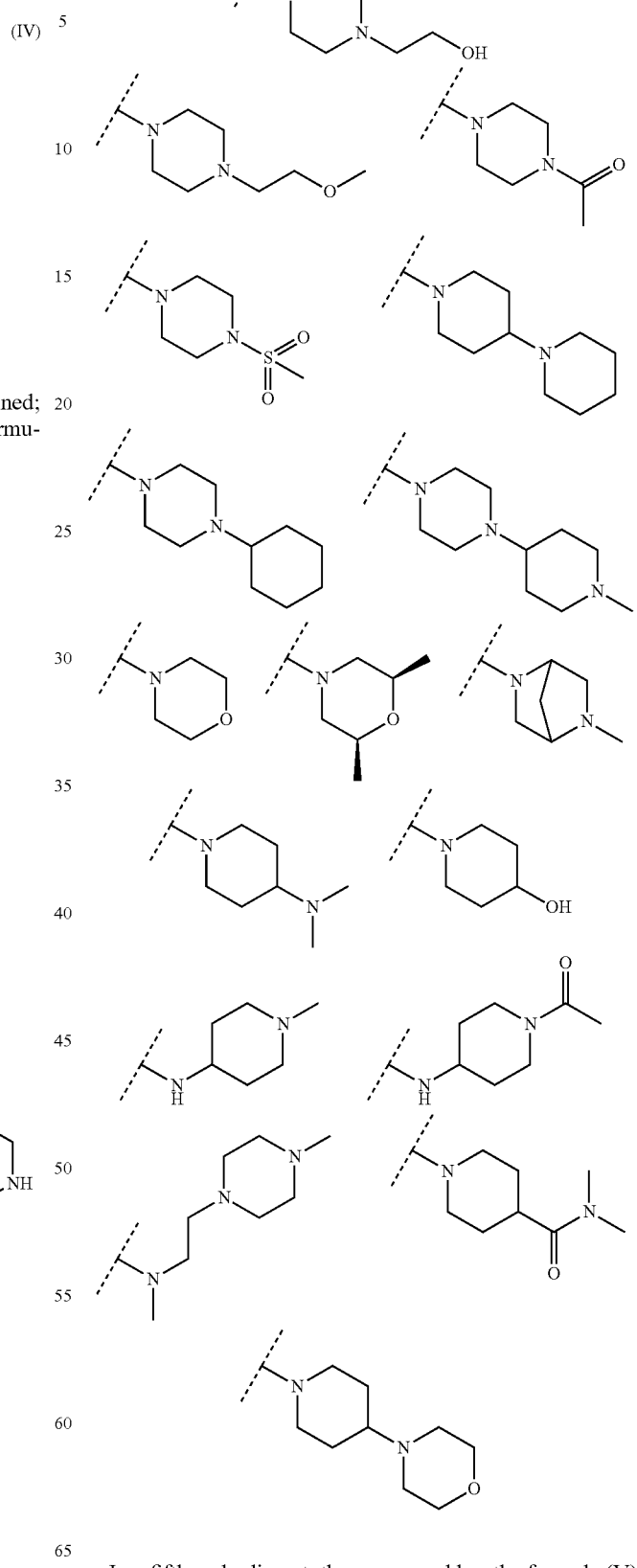
In a fifth embodiment, the compound has the formula (V) illustrated below, or its geometric isomers, enantiomers, diastereomers, racemates, pharmaceutically acceptable salts, prodrugs and solvates thereof:

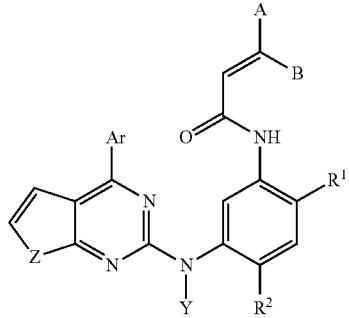

(V)

wherein A, B, Ar, $R^1$, $R^2$, Y, and Z are as previous defined: preferred examples of $R^1$ include substituents selected from the group consisting of following formulae, but are not limited to:

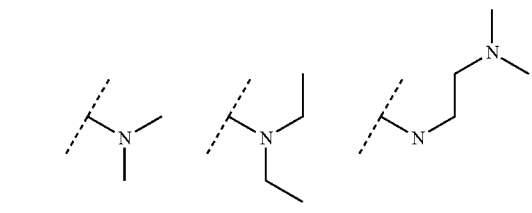

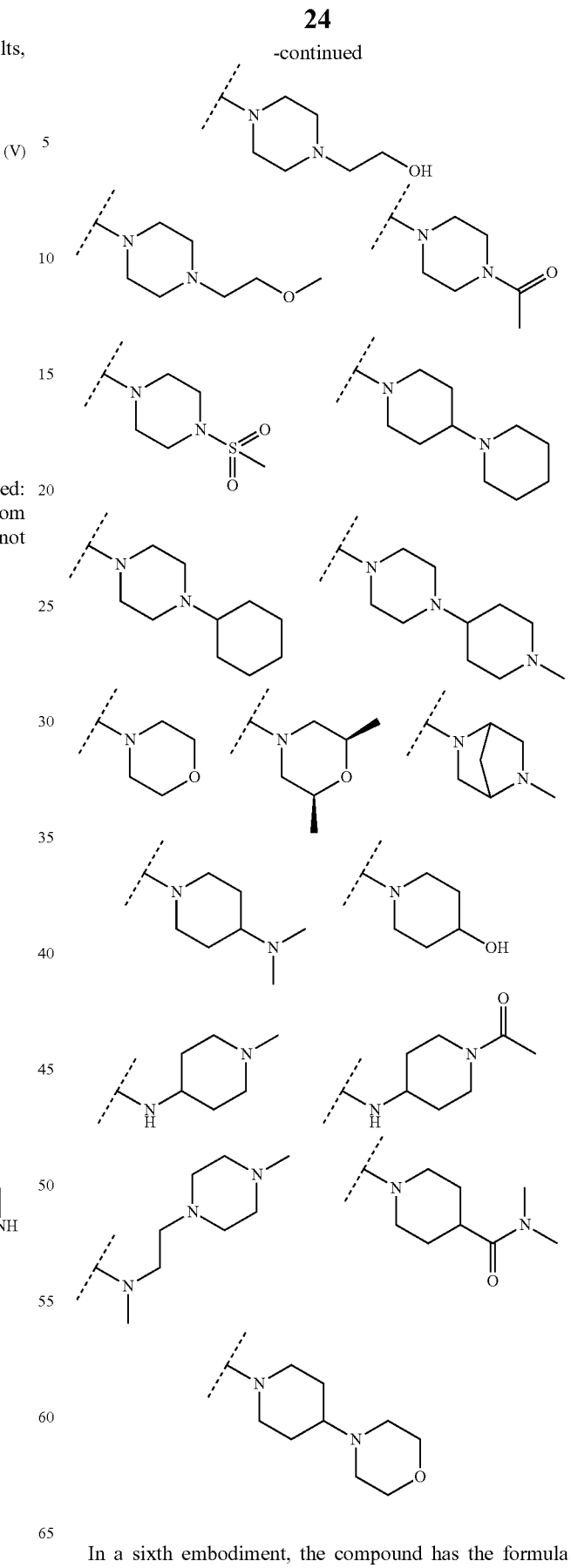

In a sixth embodiment, the compound has the formula (VI) illustrated below, or its geometric isomers, enantiomers, diastereomers, racemates, pharmaceutically acceptable salts, prodrugs and solvates thereof:

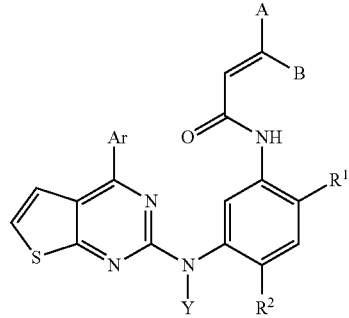

(VI)

wherein A, B, Ar, Y R$^1$, R$^2$ are as previous defined; preferred examples of R$^3$ include substituents selected from the group consisting of following formulae, but are not limited to:

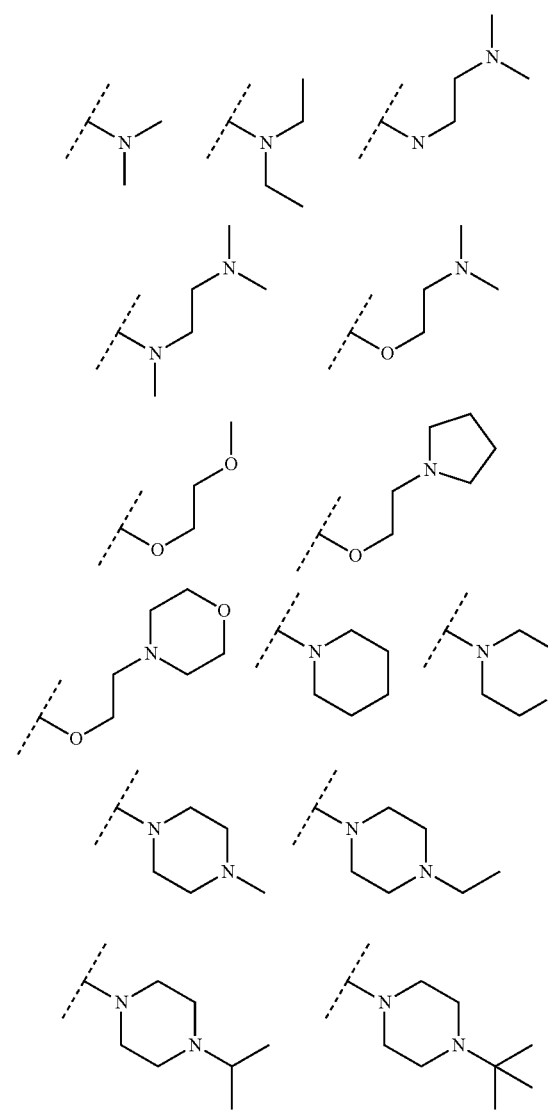

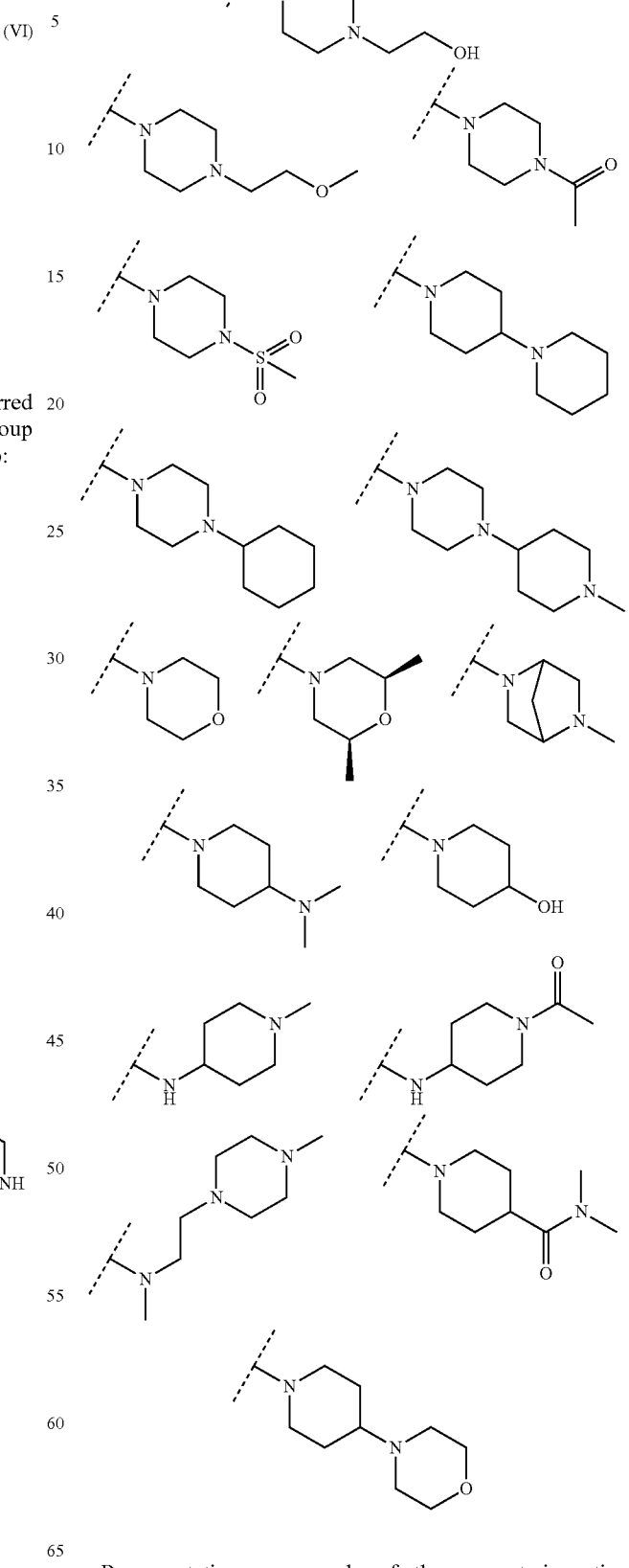

Representative compounds of the present invention include those compounds represented in Table I below or its geometric isomers, enantiomers, diastereomers, racemates, pharmaceutically acceptable salts, prodrugs and solvates thereof:
TABLE I
| Compound # | Structure |
|---|---|
| 1 | 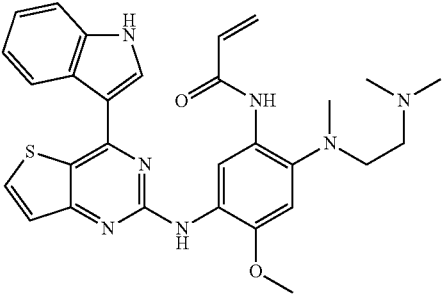 [SMILES: C=CC(=O)Nc1cc(Nc2nc(-c3c[nH]c4ccccc34)c3sccc3n2)c(OC)cc1N(C)CCN(C)C] |
| 2 | 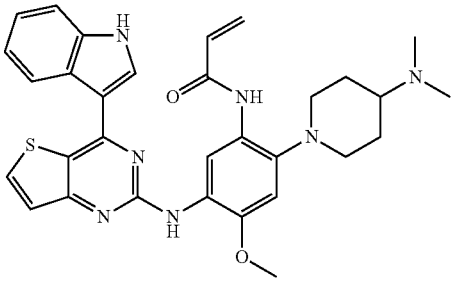 [SMILES: C=CC(=O)Nc1cc(Nc2nc(-c3c[nH]c4ccccc34)c3sccc3n2)c(OC)cc1N1CCC(N(C)C)CC1] |
| 3 | 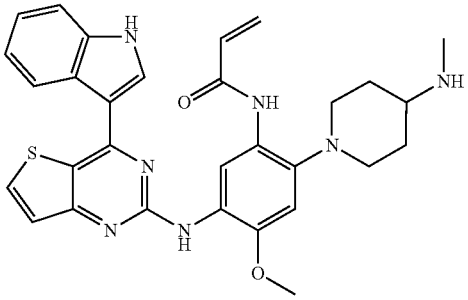 [SMILES: C=CC(=O)Nc1cc(Nc2nc(-c3c[nH]c4ccccc34)c3sccc3n2)c(OC)cc1N1CCC(NC)CC1] |
| 4 | 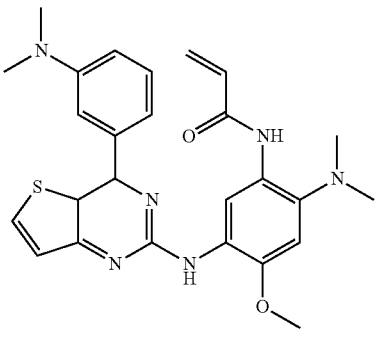 |
TABLE I-continued
| Compound # | Structure |
|---|---|
| 5 | 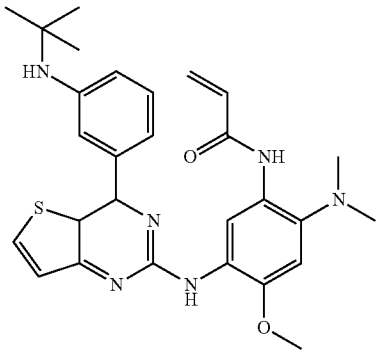 [SMILES: C=CC(=O)Nc1cc(NC2=NC(c3cccc(NC(C)(C)C)c3)C3SC=CC3=N2)c(OC)cc1N(C)C] |
| 6 | 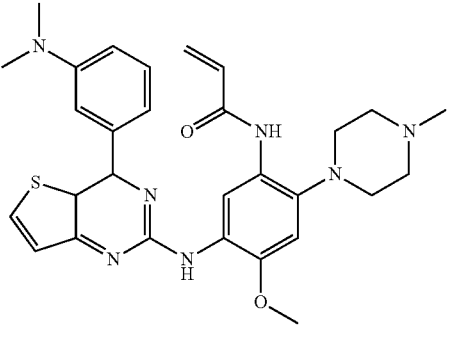 |
| 7 | 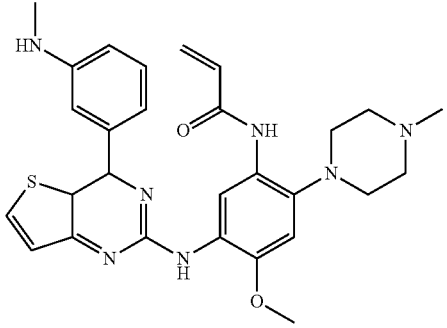 [SMILES: C=CC(=O)Nc1cc(NC2=NC(c3cccc(NC)c3)C3SC=CC3=N2)c(OC)cc1N1CCN(C)CC1] |
| 8 | 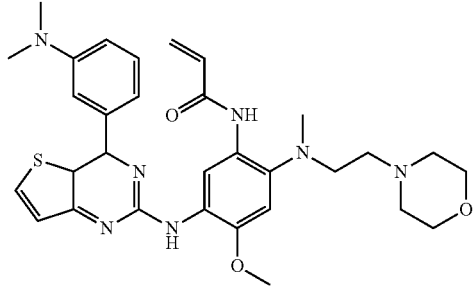 [SMILES: C=CC(=O)Nc1cc(NC2=NC(c3cccc(N(C)C)c3)C3SC=CC3=N2)c(OC)cc1N(C)CCN1CCOCC1] |

TABLE I-continued

| Compound # | Structure |
|---|---|
| 9 | *[structure image]* |
| 10 | *[structure image]* |
| 11 | *[structure image]* |
| 12 | *[structure image]* |
| 13 | *[structure image]* |
| 14 | *[structure image]* |
| 15 | *[structure image]* |
| 16 | *[structure image]* |
| 17 | *[structure image]* |

TABLE I-continued

| Compound # | Structure |
|---|---|
| 18 | (structure) |
| 19 | (structure) |
| 20 | (structure) |
| 21 | (structure) |
| 22 | (structure) |
| 23 | (structure) |
| 24 | (structure) |
| 25 | (structure) |
| 26 | (structure) |

TABLE I-continued

| Compound # | Structure |
|---|---|
| 27 | (structure) |
| 28 | (structure) |
| 29 | (structure) |
| 30 | (structure) |
| 31 | (structure) |
| 32 | (structure) |
| 33 | (structure) |
| 34 | (structure) |
| 35 | (structure) |
| 36 | (structure) |

TABLE I-continued

| Compound # | Structure |
|---|---|
| 37 | |
| 38 | |
| 39 | |
| 40 | |
| 41 | 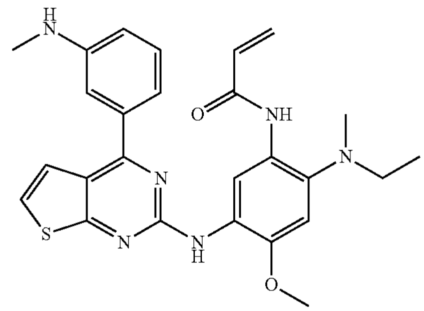 [SMILES: C=CC(=O)Nc1cc(Nc2nc(-c3cccc(NC)c3)c3ccsc3n2)c(OC)cc1N(C)CC] |
| 42 | 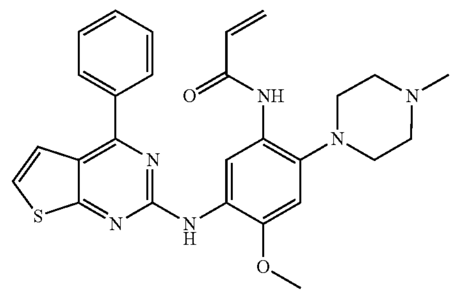 [SMILES: C=CC(=O)Nc1cc(Nc2nc(-c3ccccc3)c3ccsc3n2)c(OC)cc1N1CCN(C)CC1] |
| 43 | 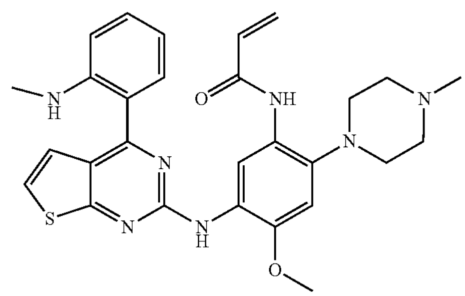 |
| 44 | 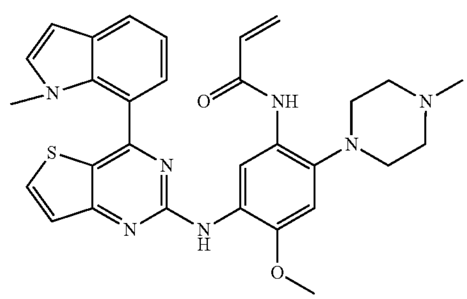 |
| 45 | 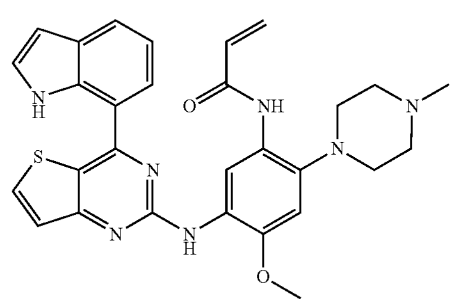 [SMILES: C=CC(=O)Nc1cc(Nc2nc(-c3cccc4cc[nH]c34)c3sccc3n2)c(OC)cc1N1CCN(C)CC1] |

TABLE I-continued

| Compound # | Structure |
|---|---|
| 46 | 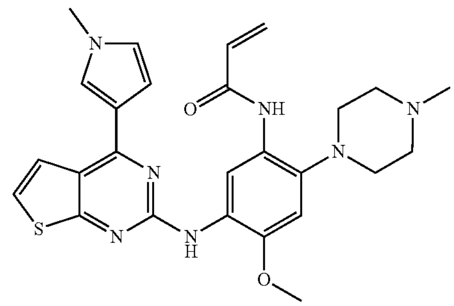 [SMILES: C=CC(=O)Nc1cc(Nc2nc(-c3ccn(C)c3)c3ccsc3n2)c(OC)cc1N1CCN(C)CC1] |
| 47 | 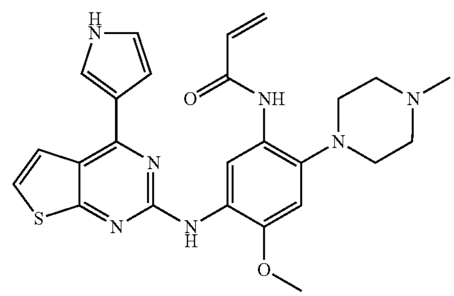 [SMILES: C=CC(=O)Nc1cc(Nc2nc(-c3cc[nH]c3)c3ccsc3n2)c(OC)cc1N1CCN(C)CC1] |
| 48 | 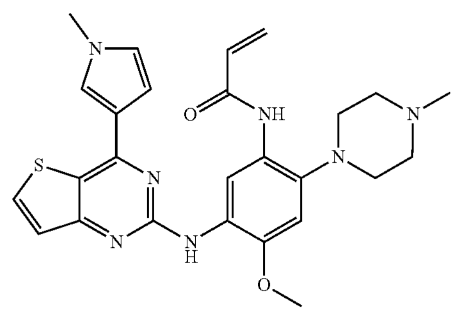 [SMILES: C=CC(=O)Nc1cc(Nc2nc(-c3ccn(C)c3)c3sccc3n2)c(OC)cc1N1CCN(C)CC1] |
| 49 | 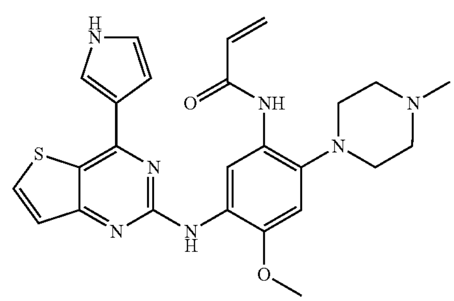 [SMILES: C=CC(=O)Nc1cc(Nc2nc(-c3cc[nH]c3)c3sccc3n2)c(OC)cc1N1CCN(C)CC1] |
| 50 | 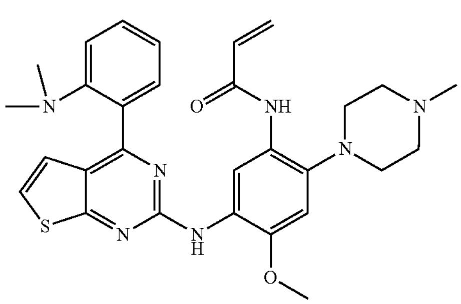 |
| 51 | 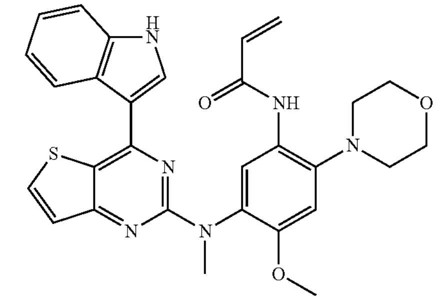 [SMILES: C=CC(=O)Nc1cc(N(C)c2nc(-c3c[nH]c4ccccc34)c3sccc3n2)c(OC)cc1N1CCOCC1] |
| 52 | 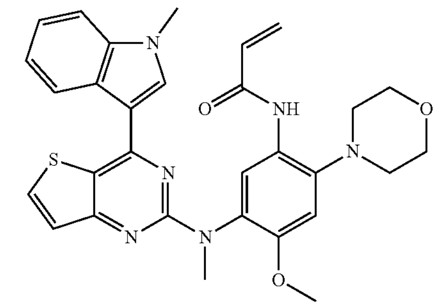 [SMILES: C=CC(=O)Nc1cc(N(C)c2nc(-c3cn(C)c4ccccc34)c3sccc3n2)c(OC)cc1N1CCOCC1] |
| 53 | 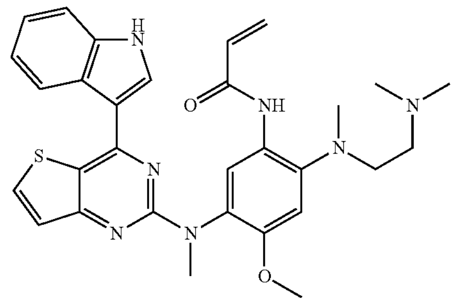 [SMILES: C=CC(=O)Nc1cc(N(C)c2nc(-c3c[nH]c4ccccc34)c3sccc3n2)c(OC)cc1N(C)CCN(C)C] |
| 54 | 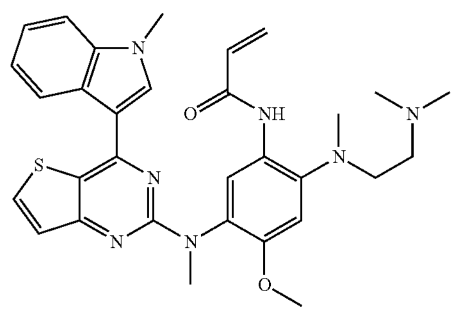 [SMILES: C=CC(=O)Nc1cc(N(C)c2nc(-c3cn(C)c4ccccc34)c3sccc3n2)c(OC)cc1N(C)CCN(C)C] |

The present invention further provides methods for the prevention or treatment of diseases or conditions involving aberrant proliferation, differentiation or survival of cells. In one embodiment, the invention further provides for the use of one or more compounds of the invention in the manufacture of a medicament for halting or decreasing diseases involving aberrant proliferation, differentiation, or survival of cells. In preferred embodiments, the disease is cancer. In one embodiment, the invention relates to a method of treating cancer in a subject in need of treatment comprising administering to said subject a therapeutically effective amount of a compound of the invention.

Compounds and compositions described herein are generally useful for the inhibition of BTK, ITK, JAK3, and EGFR etc.

The activity of a compound in this invention as a selective inhibitor may be assayed in vitro, in a cell line or in vivo. In vitro assays determine inhibition of the phosphorylation activity and subsequent functional results, or ATPase activity of activated BTK, EGFR.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In one aspect of the invention, the present invention provides for the use of one or more compounds of the invention in the manufacture of a medicament for the treatment of cancer.

In one embodiment, the present invention includes the use of one or more compounds of the invention in the manufacture of a medicament that prevents further aberrant proliferation, differentiation, or survival of cells. For example, compounds of the invention may be useful in preventing tumors from increasing in size or from reaching a metastatic state. The subject compounds may be administered to halt the progression or advancement of cancer or to induce tumor apoptosis or to inhibit tumor angiogenesis. In addition, the instant invention includes use of the subject compounds to prevent a recurrence of cancer.

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (Aurora), RAF and Aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g, MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK): Axl (e.g. Mer/Nyk, Rse); RET; and platelet-derived growth factor receptor (PDGFR) (e.g. PDGFα-R, PDGFβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. $p43^{abl}$, ARG); BTK (e.g. ITK/EMT, TEC); CSK, FAK, FPS, JAK, SRC, BMX, FER, CDK and SYK.

In another aspect of the invention, the subject compounds may be administered in combination with one or more separate agents that modulate non-kinase biological targets or processes. Such targets include histone deacetylases (HDAC), DNA methyltransferase (DNMT), heat shock proteins (e.g. Bcl-2), and proteosomes.

In a preferred embodiment, subject compounds may be combined with antineoplastic agents (e.g. small molecules, monoclonal antibodies, antisense RNA, and fusion proteins) that inhibit one or more biological targets such as Zolinza, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamnine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA)).

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

Compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (Schirmnacher et al. J. Cancer Res. Clin. Oncol., 1995, 121:487). In U.S. Pat. No. 5,484, 596, Hanna Jr. et al. claims a method for treating a resectable carcinoma to prevent recurrence or metastases, comprising surgically removing the tumor, dispersing the cells with collagenase, irradiating the cells, and vaccinating the patient with at least three consecutive doses of about 10 million cells.

In one embodiment, compounds of the invention can be used to induce or inhibit apoptosis, a physiological cell death process critical for normal development and homeostasis. Alterations of apoptotic pathways contribute to the pathogenesis of a variety of human diseases. Compounds of the invention, as modulators of apoptosis, will be useful in the treatment of a variety of human diseases with aberrations in apoptosis including cancer (particularly, but not limited to, follicular lymphomas, carcinomas with p53 mutations, hormone dependent tumors of the breast, prostate and ovary, and precancerous lesions such as familial adenomatous polyposis), viral infections (including, but not limited to, herpes virus, poxvirus, Epstein-Barr virus, Sindbis virus and adenovirus), autoimmune diseases (including, but not limited to, systemic lupus, erythematosus, immune mediated glomerulonephritis, rheumatoid arthritis, psoriasis, inflammatory bowel diseases, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including, but not limited to, churonic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

The invention provides the use of compounds of the invention for the treatment and/or prevention of immune response or immune-mediated responses and diseases, such as the prevention or treatment of rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; to treat or prevent graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treat infectious diseases causing aberrant immune response and/or activation, such as traumatic or pathogen induced immune disregulation, including for example, that which are caused by hepatitis B and C infections, HIV, *Staphylococcus aureus* infection, viral encephalitis, sepsis, parasitic diseases wherein damage is induced by an inflammatory response (e.g., leprosy); and to prevent or treat circulatory diseases, such as arteriosclerosis, atherosclerosis, vasculitis, polyarteritis nodosa and myocarditis. In addition, the present invention may be used to prevent/suppress an immune response associated with a gene therapy treatment, such as the introduction of foreign genes into autologous cells and expression of the encoded product. Thus in one embodiment, the invention relates to a method of treating an immune response disease or disorder or an immune-mediated response or disorder in a subject in need of treatment comprising administering to said subject a therapeutically effective amount of a compound of the invention.

The invention encompasses pharmaceutical compositions comprising pharmaceutically acceptable salts of the compounds of the invention as described above. The invention also encompasses pharmaceutical compositions comprising hydrates of the compounds of the invention. The term "hydrate" includes but is not limited to hemihydrate, monohydrate, dihydrate, trihydrate and the like. The invention further encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

The compounds of the invention, and derivatives, fragments, analogs, homologs, pharmaceutically acceptable salts or hydrate thereof can be incorporated into pharmaceutical compositions suitable for administration, together with a pharmaceutically acceptable carrier or excipient. Such compositions typically comprise a therapeutically effective amount of any of the compounds above, and a pharmaceutically acceptable carrier. Preferably, the effective amount when treating cancer is an amount effective to selectively induce terminal differentiation of suitable neoplastic cells and less than an amount which causes toxicity in a patient.

Compounds of the invention may be administered by any suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semisolid or liquid preparation (tablet, pellet, troche, capsule, suppository, cream, ointment, aerosol, powder, liquid, emulsion, suspension, syrup, injection etc.) containing a compound of the invention as an active ingredient, which is suitable for selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and may additionally comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens: antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

The compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, e.g., treatment for a number of consecutive days followed by a rest period. The compounds of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In one embodiment, the concentration of the compound in the patient's plasma is maintained at about 25 nM. In one embodiment, the concentration of the compound in the patient's plasma is maintained at about 50 nM. In one embodiment, the concentration of the compound in the patient's plasma is maintained at about 100 nM. In one embodiment, the concentration of the compound in the patient's plasma is maintained at about 500 nM. In one embodiment, the concentration of the compound in the patient's plasma is maintained at about 1000 nM. In one embodiment, the concentration of the compound in the patient's plasma is maintained at about 2500 nM. In one embodiment, the concentration of the compound in the patient's plasma is maintained at about 5000 nhM. The optimal amount of the compound that should be administered to the patient in the practice of the present invention will depend on the particular compound used and the type of cancer being treated.

Various terms used throughout this specification and claims, unless otherwise limited in specific instances, either individually or as part of a larger group, have the following meanings.

An "aliphatic group" or "aliphatic" is non-aromatic moiety that may be saturated (e.g. single bond) or contain one or more units of unsaturation, (e.g., double and/or triple bonds). An aliphatic group may be straight chained, branched or cyclic, contain carbon, hydrogen or, optionally, one or more heteroatoms and may be substituted or unsubstituted. An aliphatic group preferably contains between about 1 and about 24 atoms, more preferably between about 4 to about 24 atoms, more preferably between about 4-12 atoms, more typically between about 4 and about 8 atoms.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as $(C_1-C_6)$alkanoyl (e.g., formyl, acetyl, propionyl, butyryl, valeryl, caproyl, t-butylacetyl, etc.), $(C_3-C_6)$cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten carbon atoms and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten carbon atoms and more preferably about two to about eight carbon atoms. Examples of alkynyl radicals include propargyl, 1-propynyl, 2-propynyl, 1-butyne, 2-butynyl and 1-pentynyl.

The term "cycloalkyl" embraces saturated carbocyclic radicals having three to about twelve carbon atoms. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkenyl" embraces partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkoxy" embraces linear or branched oxy-containing radicals each having alkyl portions of one to about twenty carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" embraces alkyl radicals having one or more alkoxy radicals attached to the alkyl radical, that is, to form monoalkoxyalkyl and dialkoxyalkyl radicals.

The term "aryl", alone or in combination, generally means a carbocyclic aromatic system containing one, or more rings wherein such rings may be attached together in a pendent manner or may be fused. The term "aryl" embraces aromatic radicals such as phenyl, naphthyl, tetrahydronaphthyl, indane and biphenyl.

The term "carbonyl", whether used alone or with other terms, such as "alkoxycarbonyl", denotes (C=O).

The term "carbanoyl", whether used alone or with other terms, such as "arylcarbanoylyalkyl", denotes C(O)NH.

The terms "heterocyclyl", "heterocycle" "heterocyclic" or "heterocyclo" embrace saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" embraces heterocyclo-substituted alkyl radicals. More preferred heterocycloalkyl radicals are "lower heterocycloalkyl" radicals having one to six carbon atoms in the heterocyclo radicals.

The term "alkylthio" embraces radicals containing a linear or branched alkyl radical, of one to about ten carbon atoms attached to a divalent sulfur atom. Preferred alkylthio radicals have alkyl radicals of one to about twenty carbon atoms or, preferably, one to about twelve carbon atoms. More preferred alkylthio radicals have alkyl radicals are "lower alkylthio" radicals having one to about ten carbon atoms. Most preferred are alkylthio radicals having lower alkyl radicals of one to about eight carbon atoms. Examples of such lower alkylthio radicals are methylthio, ethylthio, propylthio, butylthio and hexylthio.

The terms "aralkyl" or "arylalkyl" embrace aryl-substituted alkyl radicals such as benzyl, diphenylmethyl, triphenylmethyl, phenylethyl, and diphenylethyl.

The term "aryloxy" embraces aryl radicals attached through an oxygen atom to other radicals.

The terms "aralkoxy" or "arylalkoxy" embrace aralkyl radicals attached through an oxygen atom to other radicals.

The term "aminoalkyl" embraces alkyl radicals substituted with amino radicals. Preferred aminoalkyl radicals have alkyl radicals having about one to about twenty carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, aminocarbonylcycloalkyl, aminocarbonylheterocyclyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

Chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl", "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety. The terms "halogen" or "halo" as used herein, refers to an atom selected from fluorine, chlorine, bromine and iodine.

As used herein, the term "aberrant proliferation" refers to abnormal cell growth.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The term "angiogenesis," as used herein, refers to the formation of blood vessels. Specifically, angiogenesis is a multi-step process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175-203 (1985)). Anti-angiogenic agents interfere with this process. Examples of agents that interfere with several of these steps include thrombospondin-1, angiostatin, endostatin, interferon alpha, and compounds such as matrix metalloproteinase (MMP) inhibitors that block the actions of enzymes that clear and create paths for newly forming blood vessels to follow; compounds, such as .alpha.v.beta.3 inhibitors, that interfere with molecules that blood vessel cells use to bridge between a parent blood vessel and a tumor; agents, such as specific COX-2 inhibitors, that prevent the growth of cells that form new blood vessels; and protein-based compounds that simultaneously interfere with several of these targets.

The term "apoptosis" as used herein refers to programmed cell death as signaled by the nuclei in normally functioning human and animal cells when age or state of cell health and condition dictates. An "apoptosis inducing agent" triggers the process of programmed cell death.

The term "cancer" as used herein denotes a class of diseases or disorders characterized by uncontrolled division of cells and the ability of these cells to invade other tissues, either by direct growth into adjacent tissue through invasion or by implantation into distant sites by metastasis.

The term "compound" is defined herein to include pharmaceutically acceptable salts, solvates, hydrates, polymorphs, enantiomers, diastereoisomers, racemates and the like of the compounds having a formula as set forth herein.

The term "devices" refers to any appliance, usually mechanical or electrical, designed to perform a particular function.

As used herein, the term "dysplasia" refers to abnormal cell growth, and typically refers to the earliest form of pre-cancerous lesion recognizable in a biopsy by a pathologist.

As used herein, the term "effective amount of the subject compounds," with respect to the subject method of treatment, refers to an amount of the subject compound which, when delivered as part of desired dose regimen, brings about, e.g. a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents.

The term "hyperplasia," as used herein, refers to excessive cell division or growth.

The phrase an "immunotherapeutic agent" refers to agents used to transfer the immunity of an immune donor, e.g., another person or an animal, to a host by inoculation. The term embraces the use of serum or gamma globulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "metastasis," as used herein, refers to the migration of cancer cells from the original tumor site through the blood and lymph vessels to produce cancers in other tissues. Metastasis also is the term used for a secondary cancer growing at a distant site.

The term "neoplasm," as used herein, refers to an abnormal mass of tissue that results from excessive cell division. Neoplasms may be benign (not cancerous), or malignant (cancerous) and may also be called a tumor. The term "neoplasia" is the pathological process that results in tumor formation.

As used herein, the term "pre-cancerous" refers to a condition that is not malignant, but is likely to become malignant if left untreated.

The term "proliferation" refers to cells undergoing mitosis.

The phrase a "radio therapeutic agent" refers to the use of electromagnetic or particulate radiation in the treatment of neoplasia.

The term "recurrence" as used herein refers to the return of cancer after a period of remission. This may be due to incomplete removal of cells from the initial cancer and may occur locally (the same site of initial cancer), regionally (in vicinity of initial cancer, possibly in the lymph nodes or tissue), and/or distally as a result of metastasis.

The term "treatment" refers to any process, action, application, therapy, or the like, wherein a mammal, including a human being, is subject to medical aid with the object of improving the mammal's condition, directly or indirectly.

The term "vaccine" includes agents that induce the patient's immune system to mount an immune response against the tumor by attacking cells that express tumor associated antigens (Teas).

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical *Sciences,* 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development", Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "pre-cancerous" refers to a condition that is not malignant, but is likely to become malignant if left untreated.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P.G.M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers and/or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha-($\alpha$), beta-($\beta$) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43,650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Synthetic Methods

A pyrimidine derivative of the formula I, or a pharmaceutically-acceptable salt thereof, may be prepared by any process known to be applicable to the preparation of chemically-related compounds. Suitable processes for making certain intermediates. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of a chemist.

The compounds described herein will be better understood in connection with the following representative synthetic schemes that illustrate the methods by which the compounds of the invention may be prepared, which are intended as an illustration only and not limiting of the scope of the invention.

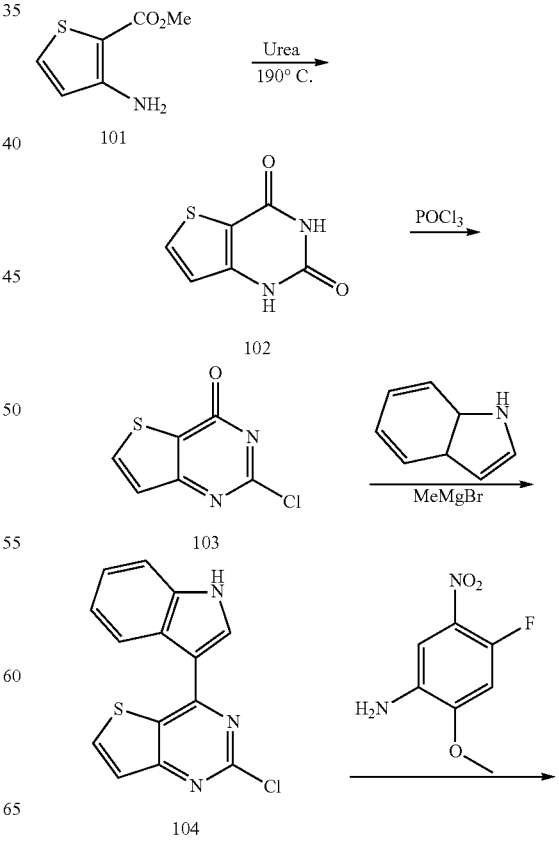

-continued

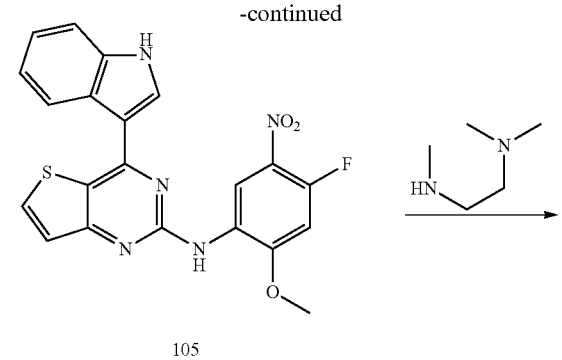

105

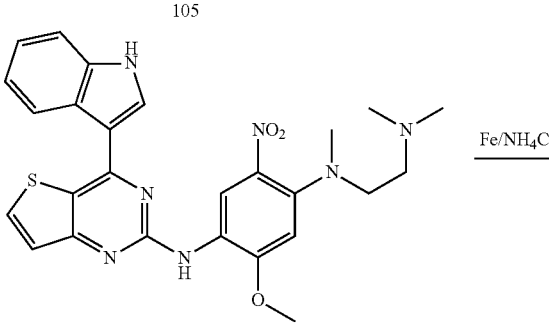

106

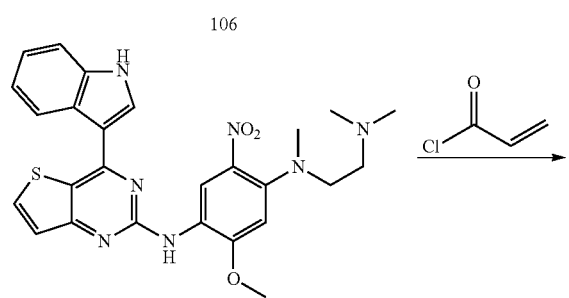

107

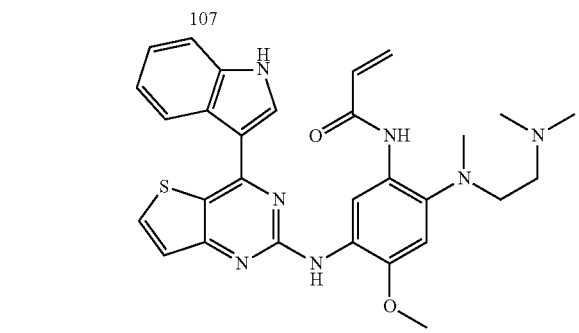

1

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1: Synthesis of N-[2-[2-(dimethylamino) ethyl-methyl-amino]-5-[[4-(1H-indol-3-yl)thieno[3, 2-d]pyrimidin-2-yl]amino]-4-methoxy-phenyl]prop-2-enamide (Compound 1)

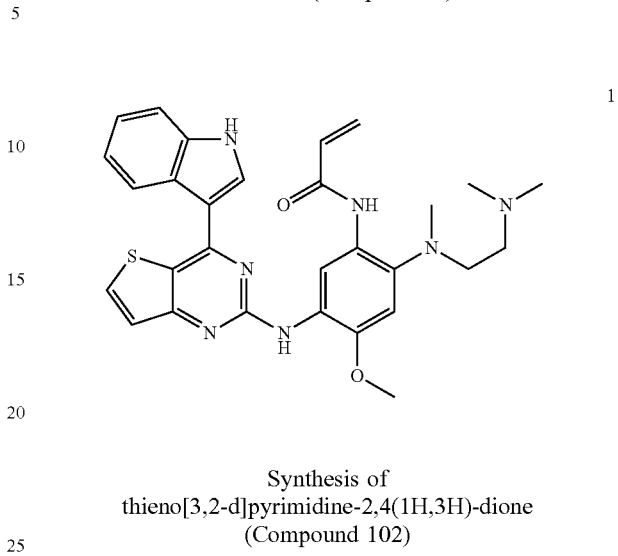

1

Synthesis of thieno[3,2-d]pyrimidine-2,4(1H,3H)-dione (Compound 102)

A mixture of methyl 3-amino-2-thiophenecarboxylate (13.48 g, 85.85 mmol) and urea (29.75 g, 0.43 mol) was heated at 190° C. for 2 h. Then the hot reaction mixture was poured into sodium hydroxide solution and insoluble material was removed by filtration. The mixture was then acidified by 2 N of HCl solution, collected by filtration and air dried, to give title compound (9.62 g, 67%) as a white precipitate.

Synthesis of 2,4-Dichlorothieno[3,2-d]pyrimidine (Compound 103)

Compound 102 (8.5 g) was suspended in phosphorous oxychloride (130 mL). The mixture was heated at 100° C. for 10 h. POCl3 was removed under reduced pressure. The mixture was dissolved in dichloromethane and quenched with ice. The product was collect by extraction with dichloromethane. The combined organic layers were dried over MgSO4 and concentrated to give product 103 as a white solid. LCMS: 205 [M+1]$^+$; $^1$H NMR (400 MHz, CDCl$_3$): δ 7.48 (d, J=5.6 Hz, 1H), 8.05 (d, J=5.6 Hz, 1H).

Synthesis of 2-chloro-4-indol-3-ylthiopheno [3,2-d]pyrimidine (Compound 104)

To a solution of indole (14 g, 120 mmol, 2 eq) in dry THF (60 mL) was added drop wise a mixture of methylmagnesium bromide (60 mL, 120 mmol, 2N, 2 eq) in THF below 5° C. and then the mixture was stirred at this temperature for 30 min. Then the suspension of 2,4-dichlorothiopheno[3,2-d]pyrimidine (12.4 g, 60 mmol, 1 eq) in 50 mL THF was added into the mixture below 5° C., and the mixture was stirred for 1 h, and then heated to 60° C. overnight. The reaction was quenched with acetic acid (8 mL, 13 mmol) and followed by addition of the water (100 mL). The precipitated solid was collected by filtration, washed with water, dried under vacuum to afford the product (9 g, 53%).

$^1$H NMR (300 MHz, DMSO-d6): δ12.22 (br, 1H), 8.59~8.66 (m, 1H), 8.51~8.53 (m, 1H), 8.42 (m, 1H), 7.50~7.61 (m, 2H), 7.23~7.38 (m, 2H);

MS Calcd. 285.0 MS Found: 286.0 ([M±H]$^+$).

Synthesis of (4-Fluoro-2-methoxy-5-nitro-phenyl)-[4-(1H-indol-3-yl)-thieno [3, 2-d] pyrimidin-2-yl]-amine (Compound 105)

p-Toluenesulfonic acid hydrate (1.4 g, 8.4 mmol, 1.2 eq) was added in one portion to a mixture of compound 104 (2 g, 7 mmol, 1 eq) and 4-fluoro-2-methoxy-5-nitroaniline (1.3 g, 7 mmol, 1 eq) in 2-pentanol (50 mL). The mixture was stirred at 130° C. overnight and then cooled to r.t. The precipitate was collected by filtration, washed with 2-pentanol (5 mL) and dried under vacuum to give some of the desired product as a yellow solid. The solid was recycled with MeOH to afford 0.9 g target compound 105.

$^1$H NMR (400 MHz, DMSO-d6): δ 12.00 (s, 1H), 9.10 (d, J=8.4 Hz, 1H), 8.53 (d, J=8.4 Hz, 1H), 8.42 (s, 1H). 8.33~8.34 (m, 2H), 7.53 (d, J=8.4 Hz, 1H), 7.37~7.41 (m, 2H), 7.25 (m, 1H), 7.15 (m, 1H), 4.04 (s, 3H); MS Calcd. 435.1 MS Found: 436.1 ([M+H]$^+$).

Synthesis of N4-[2-(dimethylamino)ethyl]-N1-[4-(1H-indol-3-yl)thieno[3,2-d]pyrimidin-2-yl]-2-methoxy-N4-methyl-5-nitro-benzene-1,4-diamine (Compound 106)

To a solution of compound 105 (220 mg) and N1,N1,N1-trimethylethane-1,2-diamine (52 mg) in DMF (4 ml) was added DIPEA (132 mg). The mixture was heated to 140° C. for 4 hours. The resulting mixture was cooled to room temperature and poured into water (10 ml), extracted with ethyl acetate (20 ml×3). The combined organic phases was washed with water, brine, dried with Na$_2$SO$_4$, filtered, and concentrated. The residue was purified by flash column to give a reddish solid (190 mg, 75% yield)

Synthesis of N1-[2-(dimethylamino)ethyl]-N4-[4-(1H-indol-3-yl)thieno[3,2-d]pyrimidin-2-yl]-5-methoxy-N1-methyl-benzene-1,2,4-triamine (Compound 107)

To a mixture of compound 106 (180 mg, 0.35 mmol), iron (78 mg, 1.4 mmol), and NH$_4$Cl (1.4 mmol) was added a mixed solution of ethanol (4 ml) and water (2 ml). The resulting mixture was refluxed for 2 hours. The mixture was cooled to room temperature, filtered, concentrated. The residue was partitioned between DCM and water. The organic phase was washed with water, brine, and dried over Na$_2$SO$_4$, filtered, concentrated to give a crude product which was used in the next step directly without further purification.

Synthesis of N-[2-[2-(dimethylamino)ethyl-methyl-amino]-5-[[4-(1H-indol-3-yl)thieno[3,2-d]pyrimidin-2-yl]amino]-4-methoxy-phenyl]prop-2-enamide (Compound 1)

To a solution of compound 107 (90 mg, 0.18 mmol) in DCM (2 ml) was added DIPEA (0.22 mmol) at 0° C. followed by addition of acryloyl chloride (0.22 mmol). The mixture was stirred for 1 hour. The mixture was diluted with DCM (4 ml) and treated with NaHCO$_3$, extracted with DCM (3 ml×2). The combined organic phases was washed with water, brine, dried over Na$_2$SO$_4$, filtered, and concentrated. The residue was purified by flash column chromatography eluting with DCM/methanol=40/1 to give the desired product (30 mg, 33% yield).

$^1$H NMR (400 MHz, DMSO-d6): δ 12.0 (s, 1H), 10.2 (s, 1H), 8.85 (s, 1H), 8.52 (s, 1H), 8.28-8.32 (m, 3H), 7.53-7.56 (m, 1H), 7.36-7.38 (m, 1H), 7.26 (t, J=7.2 Hz, 1H), 7.13 (t, J=7.2 Hz, 1H), 6.92 (s, 1H), 6.32-6.46 (m, 2H), 5.69-5.73 (m, 1H), 4.01 (s, 3H), 2.89 (m, 2H), 2.69 (s, 3H), 2.33 (m, 2H), 2.26 (s, 6H). MS Calcd: 541.6 MS Found: 542.6 ([M+H]$^+$).

BIOLOGICAL ASSAYS

As stated hereinbefore the derivatives defined in the present invention possess anti-proliferation activity. These properties may be assessed, for example, using one or more of the procedures set out below:

1. BTK Enzyme Assay

The following TABLE II lists compounds representative of the invention and their activity in BTK assays. In these assays, the following grading was used: A: >30% inhibition @1 μM; B: <30% inhibition @1 μM.

TABLE II

| Compound # | BTK (% inh @ 1 uM) |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | B |
| 18 | B |
| 19 | B |
| 20 | B |
| 21 | A |
| 22 | A |
| 23 | A |
| 24 | A |
| 25 | B |
| 26 | A |
| 27 | A |
| 28 | B |
| 29 | B |
| 30 | A |
| 31 | B |
| 32 | A |
| 33 | B |
| 34 | B |
| 35 | B |
| 36 | A |
| 37 | A |
| 38 | A |
| 39 | A |
| 40 | B |
| 41 | A |
| 42 | B |
| 43 | B |
| 44 | A |
| 45 | B |
| 46 | A |
| 47 | B |
| 48 | A |
| 49 | A |
| 50 | A |
| 51 | B |
| 52 | B |

TABLE II-continued

| Compound # | BTK (% inh @ 1 uM) |
|---|---|
| 53 | A |
| 54 | B |

2. EGFR Enzyme Assay

The following TABLE III lists compounds representative of the invention and their activity in EGFR assays. In these assays, the following grading was used: A: >50% @1 μM; B: <50% @ 1 μM.

TABLE III

| Compound # | T790M (% inh @ 1 uM) |
|---|---|
| 1 | A |
| 2 | A |
| 5 | A |
| 6 | B |
| 9 | B |
| 10 | A |
| 18 | A |
| 24 | B |
| 26 | B |
| 35 | A |
| 36 | B |
| 37 | A |
| 41 | A |
| 43 | B |
| 50 | B |
| 52 | B |

The invention has been illustrated by the above descriptions and examples. The example are not intended to be limiting in any way. As used throughout, ranges are used as shorthand for describing each and every value that is within the range. Any value within the range can be selected as the terminus of the range. It is understood that when formulations are described, they may be described in terms of their ingredients, as is common in the art, notwithstanding that these ingredients may react with one another in the actual formulation as it is made, stored and used, and such products are intended to be covered by the formulations described. In addition, all references cited herein are hereby incorporated by reference in their entireties.

What is claimed is:

1. A compound of formula (I):

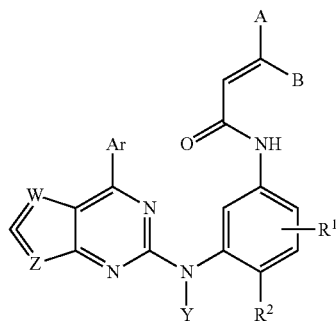

(I)

or a geometric isomer, a pharmaceutically acceptable salt, prodrug or solvate thereof, wherein Ar is aryl; substituted aryl; heteroaryl; substituted heteroaryl; heterocyclyl, cycloalkenyl, cycloalkyl aryl; aryl fused heteroaryl; heteroaryl fused aryl; straight or branched, substituted or unsubstituted alkyl aryl or heteroaryl; substituted or unsubstituted alkenyl aryl or heteroaryl; substituted or unsubstituted alkynyl aryl or heteroaryl; arylakyl; arylalkenyl; arylalkynyl; heteroarylalkenyl; heteroarylalkenyl; heteroarylalkynyl;

one of W and Z is CH, and W is O, S, NH, $NR^3$ when Z is CH, and Z is O or S when W is CH, A is H, $C_{1-6}$, $-(CH_2)_nNR^4R^5$, wherein n=1-6;

B is H, $C_{1-6}$ alkyl, $-(CH_2)_nNR^4R^5$, wherein n=1-6;

$R^1$ is H, halogen, SH, OH, $NO_2$, CN, $C_{1-6}$ alkyl, $C_{1-6}$ alkoxy, $C_{1-6}$ alkoxycarbonyl, di-$C_{1-6}$ alkylamino $C_{2-6}$ alkylcarbonyl, amino, $C_{1-6}$ alkylamino, di-$C_{1-6}$ alkylamino, carbamoyl, $C_{1-6}$ alkylcarbamoyl, di($C_{1-6}$ alkyl) carbamoyl, di$C_{1-6}$ alkylamino $C_{2-6}$ alkylcarbamoyl, sulfamoyl, $C_{1-6}$ alkylsulfonyl, $C_{1-6}$ alkylsulfinyl, di$C_{1-6}$ alkylamino$C_{2-6}$ alkylsulfamoyl, di $C_{1-6}$ alkylphsophonyl $C_{1-6}$ alkyl, hydroxy$C_{2-6}$ alkoxy, hydroxycarbonyl $C_{1-6}$ alkyl, $C_{1-6}$ alkoxy $C_{1-6}$ alkyl, di$C_{1-6}$ alkylamino$C_{2-6}$ alkylamino, substituted di$C_{1-6}$ alkylamino $C_{2-6}$ alkylamino, amino $C_{1-6}$ alkyl, di$C_{1-6}$ alkylaminoacetyl, hydroxydi$C_{2-6}$ alkylamino, $C_{1-6}$ alkylamino$C_{2-6}$ alkoxy, di$C_{1-6}$ alkylamino$C_{2-6}$ alkoxy, heteroaryl, heterocycle, heterocyclic oxy, heterocyclicthio, heterocyclicsulfinyl, heterocyclic sulfonyl, heterocyclic sulfamoyl, heterocyclic $C_{1-6}$ alkyl, heterocyclic $C_{1-6}$ alkoxy, heterocyclic amino, heterocyclic $C_{1-6}$ alkylamino, heterocyclic carbonyl, heterocyclic $C_{1-6}$ alkylcarbonyl; wherein a heterocycle is saturated or partially unsaturated 3 to 8 membered cyclic or bicyclic hetero ring with one or more N, O, S, SO, and $SO_2$, in which C or the hetero atom may have one or more substituents that consists of $C_{1-6}$ alkyl, hydroxy, hydroxy $C_{1-6}$ alkyl, $C_{1-6}$ alkylcarbonyl, $C_{1-6}$ alkyl amino, di $C_{1-6}$ alkylamino;

$R^2$ is H, halogen, SH, OH, NO2, CN, $C_{1-6}$alkyl, $C_{1-6}$ alkoxy, $C_{1-6}$ alkoxycarbonyl, di$C_{1-6}$ alkylamino$C_{2-6}$ alkylcarbonyl, amino, $C_{1-6}$ alkylamino, di$C_{1-6}$ alkylamino, carbamoyl, $C_{1-6}$ alkylcarbamoyl, di($C_{1-6}$ alkyl) carbamoyl, di$C_{1-6}$ alkylamino$C_{2-6}$ alkylcarbamoyl, sulfamoyl, $C_{1-6}$ alkylsulfonyl, $C_{1-6}$ alkylsulfinyl, di$C_{1-6}$ alkylamino$C_{2-6}$ alkylsulfamoyl, di$C_{1-6}$ alkylphsophonyl$C_{1-6}$ alkyl, hydroxy$C_{2-6}$ alkoxy, hydroxycarbonyl$C_{1-6}$ alkyl, $C_{1-6}$ alkoxy$C_{1-6}$ alkyl, di$C_{1-6}$ alkylamino$C_{2-6}$ alkylamino, substituted di$C_{1-6}$ alkylamino$C_{2-6}$ alkylamino, amino$C_{1-6}$ alkyl, di$C_{1-6}$ alkylaminoacetyl, hydroxydi$C_{2-6}$ alkylamino, $C_{1-6}$ alkylamino$C_{2-6}$ alkoxy, di$C_{1-6}$ alkylamino$C_{2-6}$ alkoxy, heteroaryl, heterocycle, heterocyclic oxy, heterocyclicthio, heterocyclicsulfinyl, heterocyclic sulfonyl, heterocyclic sulfamoyl, heterocyclic $C_{1-6}$ alkyl, heterocyclic $C_{1-6}$ alkoxy, heterocyclic amino, heterocyclic $C_{1-6}$ alkylamino, heterocyclic carbonyl, heterocyclic $C_{1-6}$ alkylcarbonyl, wherein a heterocycle is saturated or partially unsaturated 3 to 8 membered cyclic or bicyclic hetero ring with one or more N, O, S, SO, and $SO_2$, in which C or the hetero atom may have one or more substituents that consists of $C_{1-6}$ alkyl, hydroxy, hydroxy $C_{1-6}$ alkyl, $C_{1-6}$ alkylcarbonyl, $C_{1-6}$ alkyl amino, di $C_{1-6}$ alkylamino;

$R^3$ is $C_{1-6}$ alkyl, hydroxy $C_{1-6}$ alkyl, $C_{1-6}$ alkylamino $C_{2-6}$ alkyl, di $C_{1-6}$ alkylamino$C_{2-6}$ alkyl, $C_{1-6}$ alkylcarbonyl;

$R^4$ is $C_{1-6}$ alkyl, hydroxy $C_{1-6}$ alkyl, $C_{1-6}$ alkylamino $C_{2-6}$ alkyl, di $C_{1-6}$ alkylamino$C_{2-6}$ alkyl, $C_{1-6}$ alkylcarbonyl; and $R^5$ is H, $C_{1-6}$ alkyl, hydroxy $C_{1-6}$ alkyl, $C_{1-6}$ alkylamino $C_{2-6}$ alkyl, di $C_{1-6}$ alkylamino$C_{2-6}$ alkyl, $C_{1-6}$ alkylcarbonyl, Y is H, $C_{1-6}$ alkyl, aryl; substituted aryl; heteroaryl; substituted heteroaryl; heterocyclyl, cycloalkenyl, or cycloalkyl aryl.

2. A compound according to claim 1, wherein W is CH.

3. A compound of claim 2 wherein Z is S.

4. A compound according to claim 1, wherein Z is CH.

5. A compound of claim 4 wherein W is S.

6. A compound according to claim 1 represented by formula (II):

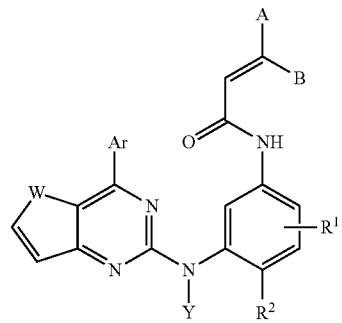

(II)

or its geometric isomers, enantiomers, diastereomers, racemates, pharmaceutically acceptable salts, prodrugs and solvates thereof.

7. A compound of claim 6, wherein R is selected from the group consisting of:

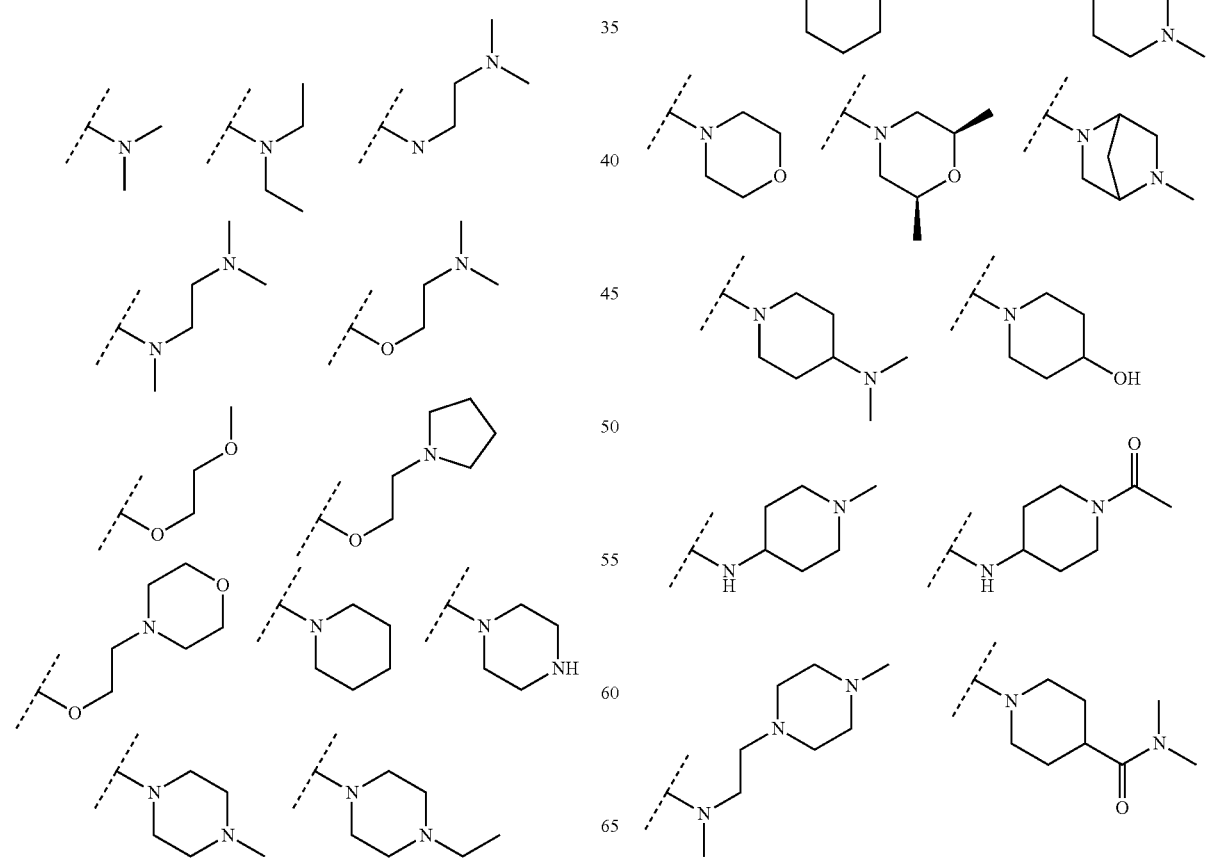

-continued

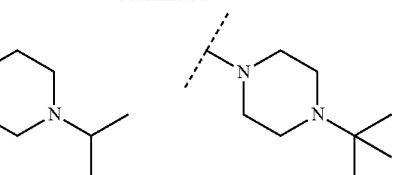
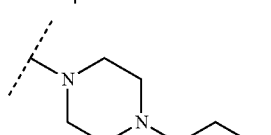
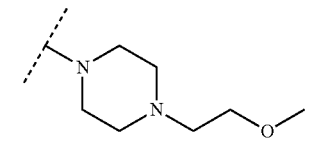
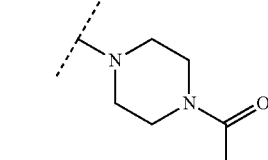
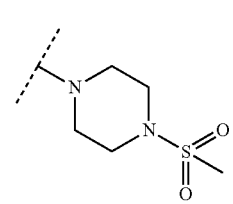
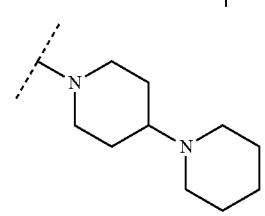
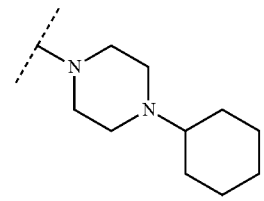
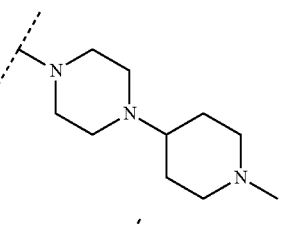
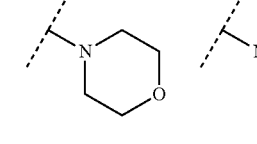
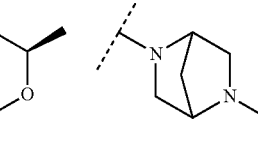
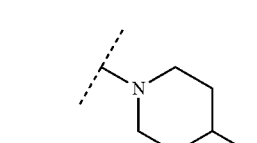
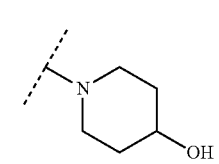
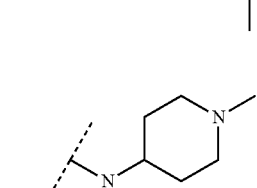
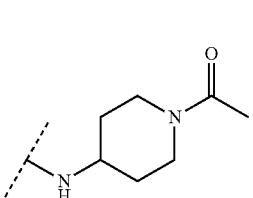
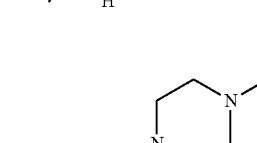
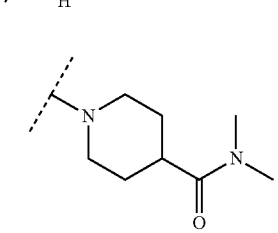

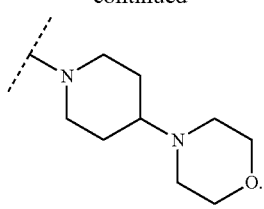
8. A compound according to claim 1 represented by formula (III):
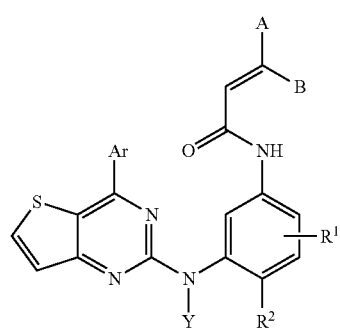
(III)
or its geometric isomers, enantiomers, diastereomers, racemates, pharmaceutically acceptable salts, prodrugs and solvates thereof.
9. A compound of claim 8, wherein R is selected from the group consisting:
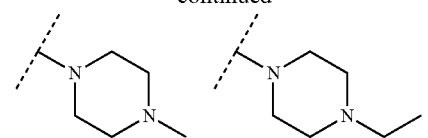
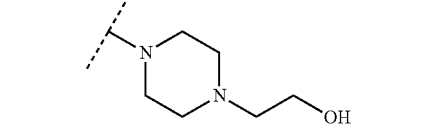
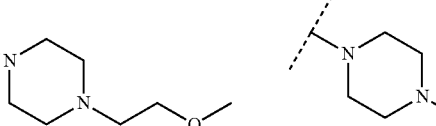
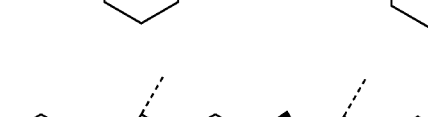
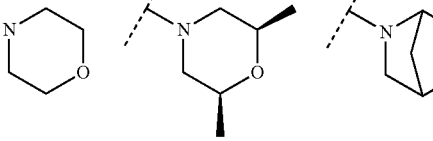
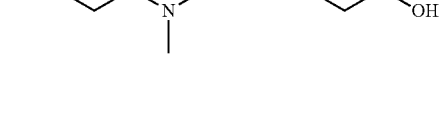

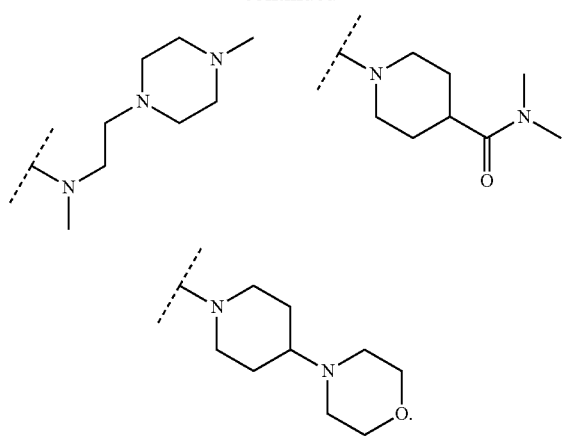
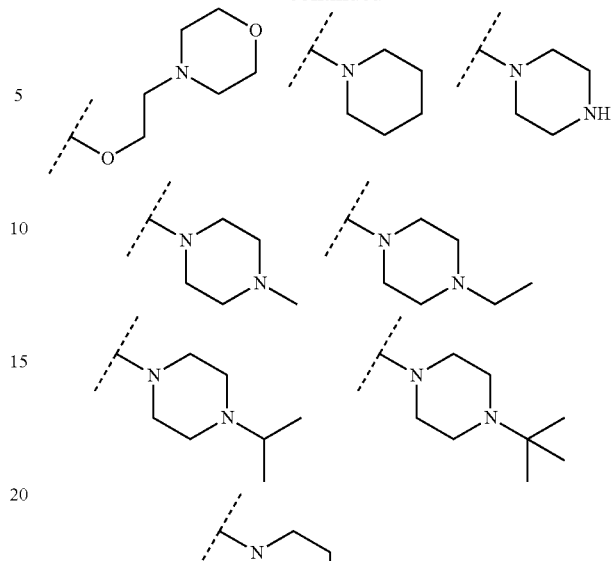
10. A compound according to claim 1, wherein the compound is represented by formula (IV):
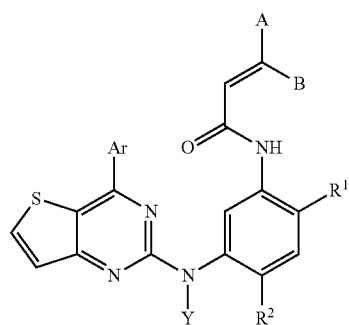
(IV)
or its geometric isomers, enantiomers, diastereomers, racemates, pharmaceutically acceptable salts, prodrugs and solvates thereof.
11. A compound of claim 10, wherein $R^1$ is selected from the group consisting of:
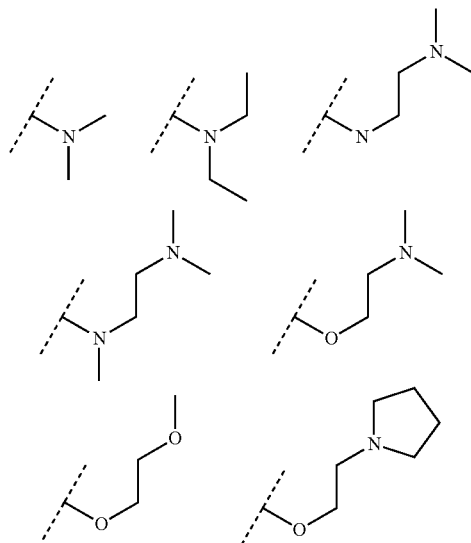
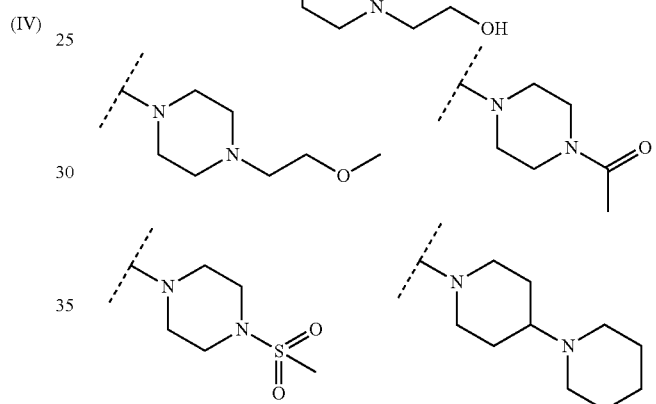
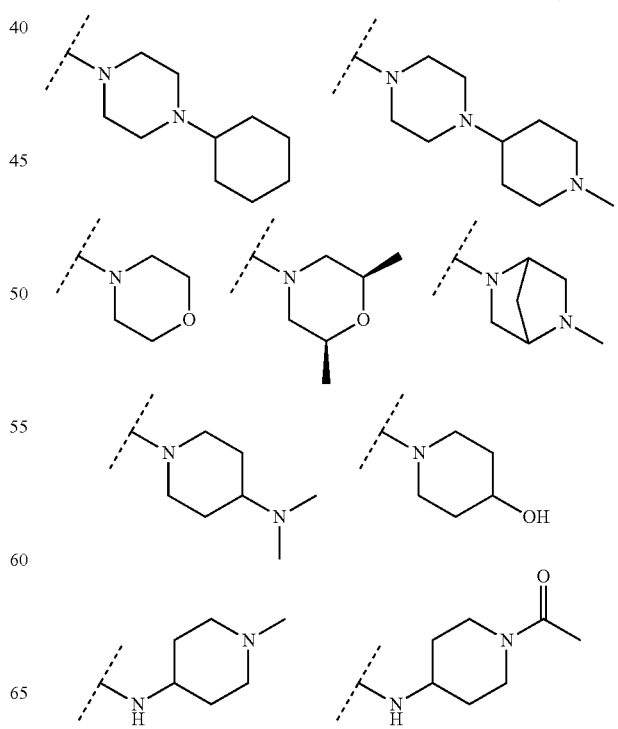

-continued
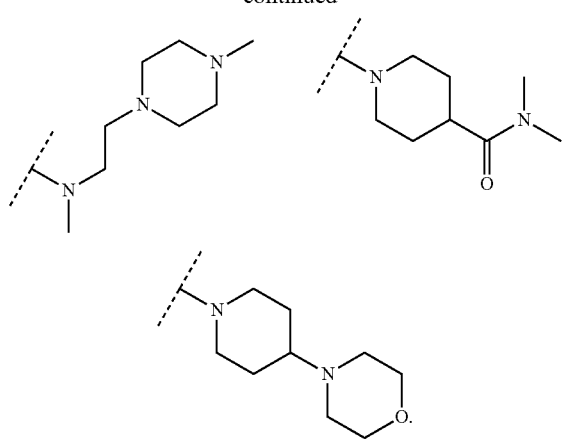
12. A compound according to claim 1, wherein the compound is represented by formula (V):
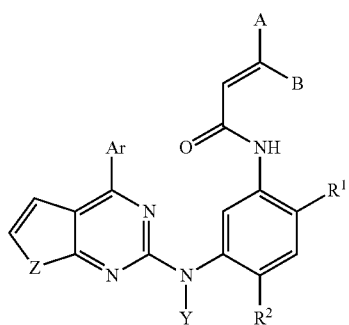
(V)
or its geometric isomers, enantiomers, diastereomers, racemates, pharmaceutically acceptable salts, prodrugs and solvates thereof.
13. A compound of claim 12, wherein R is selected from the group consisting of:
-continued
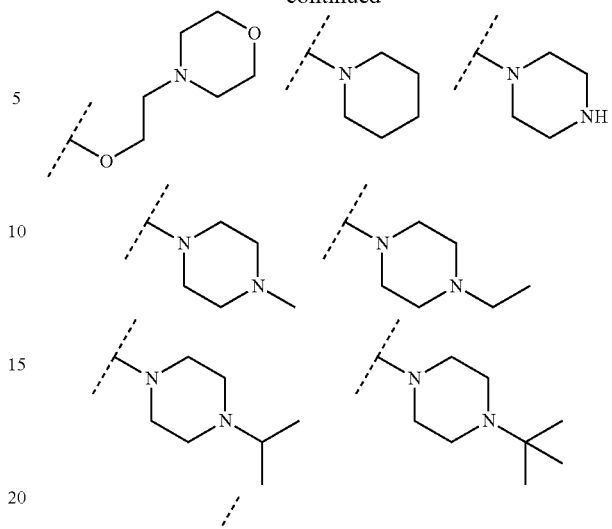
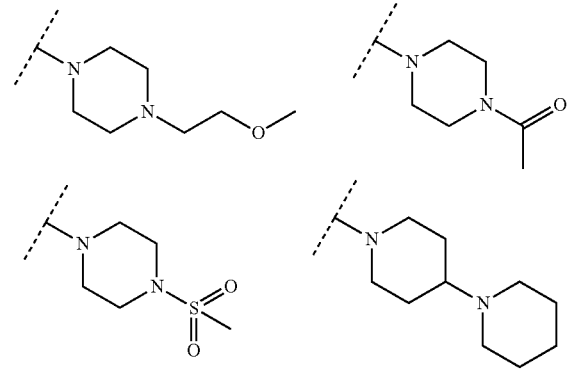
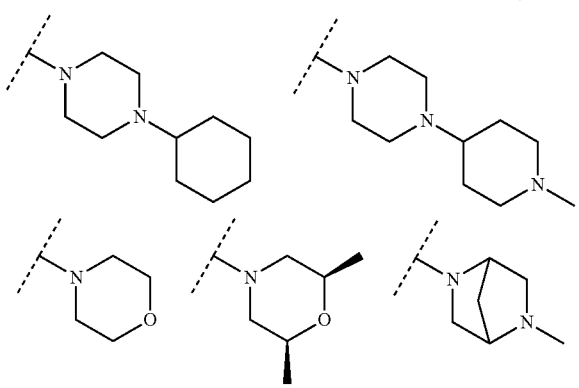
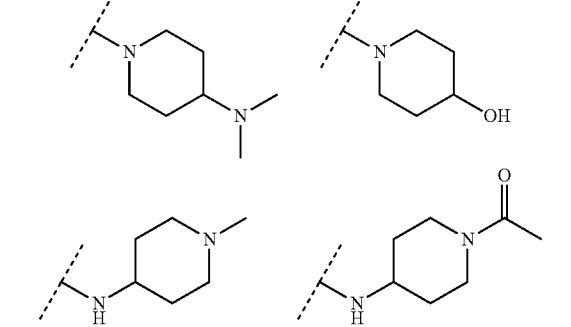

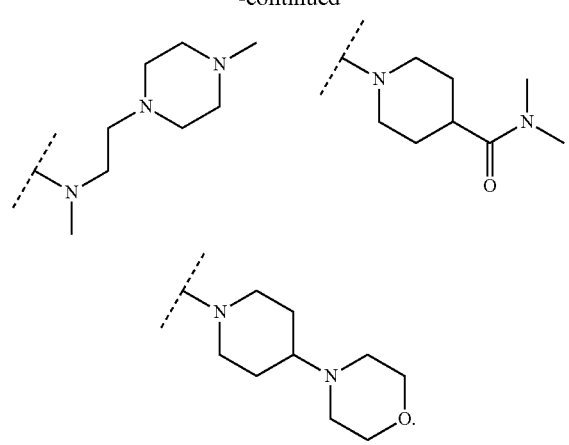
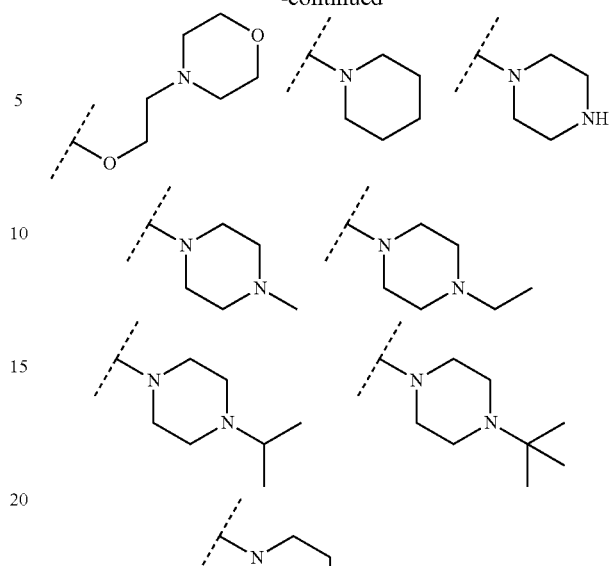
14. A compound according to claim 1 represented by formula (VI):
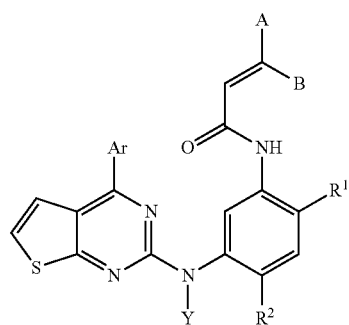
(VI)
or its geometric isomers, enantiomers, diastereomers, racemates, pharmaceutically acceptable salts, prodrugs and solvates thereof.
15. A compound of claim 14, wherein R is selected from the group consisting of:
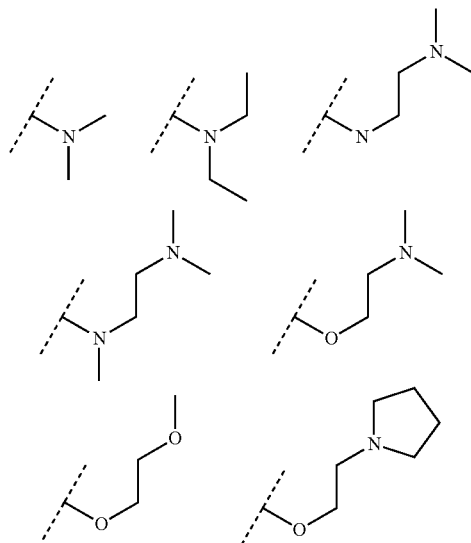
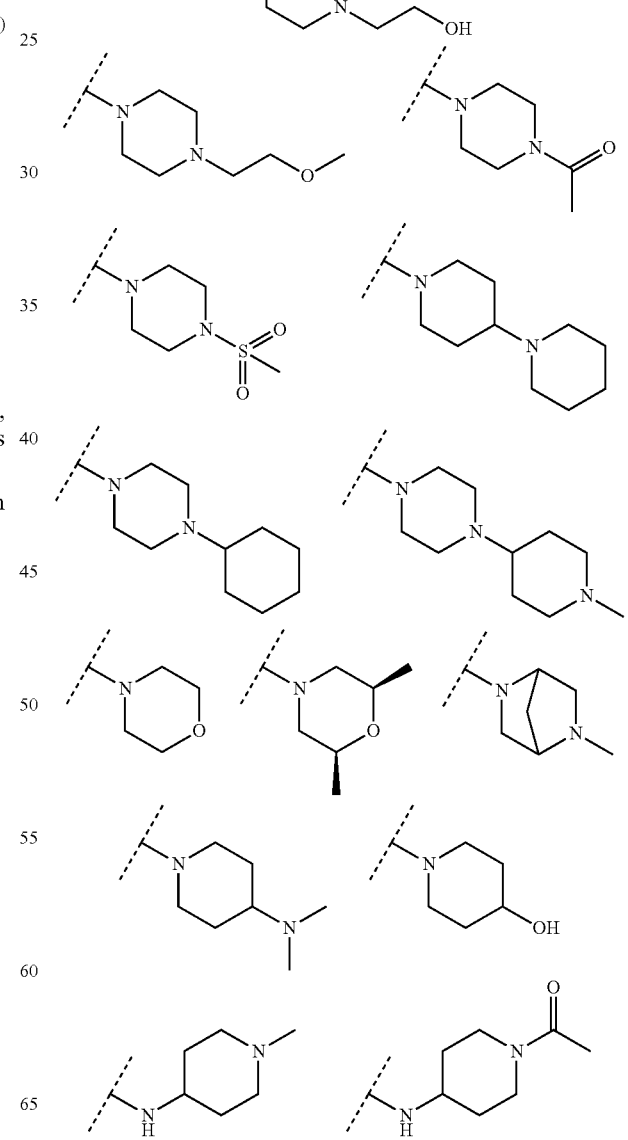

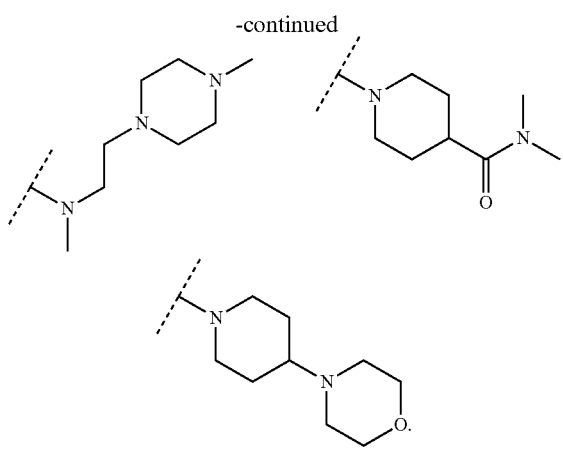

16. A compound according to claim 1, selected from the group consisting of 1: N-[2-[2-(dimethylamino)ethyl-methyl-amino]-5-[[4-(1H-indol-3-yl)thieno[3,2-d]pyrimidin-2-yl]amino]-4-methoxy-phenyl]prop-2-enamide,
2: N-[2-[4-(dimethylamino)-1-piperidyl]-5-[[4-(1H-indol-3-yl)thieno[3,2-d]pyrimidin-2-yl]amino]-4-methoxy-phenyl]prop-2-enamide,
3: N-[5-[[4-(1H-indol-3-yl)thieno[3,2-d]pyrimidin-2-yl]amino]-4-methoxy-2-[4-(methylamino)-1-piperidyl]phenyl]prop-2-enamide,
4: N-[2-(dimethylamino)-5-[[4-[3-(dimethylamino)phenyl]-4,4a-dihydrothieno[3,2-d]pyrimidin-2-yl]amino]-4-methoxy-phenyl]prop-2-enamide,
5: N-[5-[[4-[3-(tert-butylamino)phenyl]-4,4a-dihydrothieno[3,2-d]pyrimidin-2-yl]amino]-2-(dimethylamino)-4-methoxy-phenyl]prop-2-enamide,
6: N-[5-[[4-[3-(dimethylamino)phenyl]-4,4a-dihydrothieno[3,2-d]pyrimidin-2-yl]amino]-4-methoxy-2-(4-methylpiperazin-1-yl)phenyl]prop-2-enamide,
7: N-[4-methoxy-5-[[4-[3-(methylamino)phenyl]-4,4a-dihydrothieno[3,2-d]pyrimidin-2-yl]amino]-2-(4-methylpiperazin-1-yl)phenyl]prop-2-enamide,
8: N-[5-[[4-[3-(dimethylamino)phenyl]-4,4a-dihydrothieno[3,2-d]pyrimidin-2-yl]amino]-4-methoxy-2-[methyl(2-morpholinoethyl)amino]phenyl]prop-2-enamide,
9: N-[4-methoxy-5-[[4-[3-(methylamino)phenyl]-4,4a-dihydrothieno[3,2-d]pyrimidin-2-yl]amino]-2-[methyl(2-morpholinoethyl)amino]phenyl]prop-2-enamide,
10: N-[5-[[4-[3-(dimethylamino)phenyl]-4,4a-dihydrothieno[3,2-d]pyrimidin-2-yl]amino]-4-methoxy-2-morpholino-phenyl]prop-2-enamide,
11: N-[5-[[4-[3-(tert-butylamino)phenyl]-4,4a-dihydrothieno[3,2-d]pyrimidin-2-yl]amino]-4-methoxy-2-morpholino-phenyl]prop-2-enamide,
12: N-[2-[2-(dimethylamino)ethoxy]-5-[[4-[3-(dimethylamino)phenyl]-4,4a-dihydrothieno[3,2-d]pyrimidin-2-yl]amino]-4-methoxy-phenyl]prop-2-enamide,
13: N-[2-[2-(dimethylamino)ethoxy]-4-methoxy-5-[[4-[3-(methylamino)phenyl]-4,4a-dihydrothieno[3,2-d]pyrimidin-2-yl]amino]phenyl]prop-2-enamide,
14: N-[5-[[4-[3-(dimethylamino)phenyl]-4,4a-dihydrothieno[3,2-d]pyrimidin-2-yl]amino]-4-methoxy-2-[2-(1-piperidyl)ethoxy]phenyl]prop-2-enamide,
15: N-[4-methoxy-5-[[4-[3-(methylamino)phenyl]-4,4a-dihydrothieno[3,2-d]pyrimidin-2-yl]amino]-2-[2-(1-piperidyl)ethoxy]phenyl]prop-2-enamide,
16: 1-[4-[[4-[3-(dimethylamino)phenyl]-4,4a-dihydrothieno[3,2-d]pyrimidin-2-yl]amino]-5-methoxy-2-(prop-2-enoylamino)phenyl]-N,N-dimethyl-piperidine-4-carboxamide,
17: 1-[5-methoxy-4-[[4-[3-(methylamino)phenyl]-4,4a-dihydrothieno[3,2-d]pyrimidin-2-yl]amino]-2-(prop-2-enoylamino)phenyl]-N,N-dimethyl-piperidine-4-carboxamide,
18: N-[4-methoxy-2-(4-methylpiperazin-1-yl)-5-[(4-phenyl-4,4a-dihydrothieno[3,2-d]pyrimidin-2-yl)amino]phenyl]prop-2-enamide,
19: N-[5-[[4-(3-aminophenyl)-4,4a-dihydrothieno[3,2-d]pyrimidin-2-yl]amino]-4-methoxy-2-(4-methylpiperazin-1-yl)phenyl]prop-2-enamide,
20: N-[2-[4-(dimethylamino)-1-piperidyl]-4-methoxy-5-[[4-(3-methoxyphenyl)-4,4a-dihydrothieno[3,2-d]pyrimidin-2-yl]amino]phenyl]prop-2-enamide,
21: N-[5-[[4-(1H-indol-3-yl)thieno[3,2-d]pyrimidin-2-yl]amino]-4-methoxy-2-(4-methylpiperazin-1-yl)phenyl]prop-2-enamide,
22: N-[4-methoxy-5-[[4-(1-methylindol-3-yl)thieno[3,2-d]pyrimidin-2-yl]amino]-2-(4-methylpiperazin-1-yl)phenyl]prop-2-enamide,
23: N-[5-[[4-(1H-indol-3-yl)thieno[3,2-d]pyrimidin-2-yl]amino]-4-methoxy-2-morpholino-phenyl]prop-2-enamide,
24: N-[5-[[4-[3-(dimethylamino)phenyl]thieno[3,2-d]pyrimidin-2-yl]amino]-4-methoxy-2-(4-methylpiperazin-1-yl)phenyl]prop-2-enamide,
25: N-[4-methoxy-5-[[4-[4-(methylamino)phenyl]thieno[3,2-d]pyrimidin-2-yl]amino]-2-(4-methylpiperazin-1-yl)phenyl]prop-2-enamide,
26: N-[4-methoxy-2-(4-methylpiperazin-1-yl)-5-[(4-phenylthieno[3,2-d]pyrimidin-2-yl)amino]phenyl]prop-2-enamide,
27: N-[5-[[4-[4-(tert-butylamino)phenyl]thieno[3,2-d]pyrimidin-2-yl]amino]-4-methoxy-2-(4-methylpiperazin-1-yl)phenyl]prop-2-enamide,
28: N-[2-[4-(dimethylamino)-1-piperidyl]-4-methoxy-5-[[4-(3-methoxyphenyl)-5-methyl-4,4a-dihydropyrrolo[3,2-d]pyrimidin-2-yl]amino]phenyl]prop-2-enamide,
29: N-[4-methoxy-5-[[4-[2-(methylamino)phenyl]thieno[3,2-d]pyrimidin-2-yl]amino]-2-(4-methylpiperazin-1-yl)phenyl]prop-2-enamide,
30: N-[4-methoxy-2-(4-methylpiperazin-1-yl)-5-[(4-phenylthieno[3,2-d]pyrimidin-2-yl)amino]phenyl]prop-2-enamide,
31: N-[2-[2-(dimethylamino)ethyl-methyl-amino]-4-methoxy-5-[[4-[2-(methylamino)phenyl]thieno[3,2-d]pyrimidin-2-yl]amino]phenyl]prop-2-enamide,
32: N-[2-[2-(dimethylamino)ethyl-methyl-amino]-4-methoxy-5-[(4-phenylthieno[2,3-d]pyrimidin-2-yl)amino]phenyl]prop-2-enamide,
33: N-[2-[2-(dimethylamino)ethyl-methyl-amino]-4-methoxy-5-[[4-[3-(methylamino)phenyl]thieno[2,3-d]pyrimidin-2-yl]amino]phenyl]prop-2-enamide,
34: N-[4-methoxy-5-[[4-(1-methylindol-3-yl)thieno[3,2-d]pyrimidin-2-yl]amino]-2-(2-morpholinoethoxy)phenyl]prop-2-enamide,
35: N-[4-methoxy-5-[[4-[3-(methylamino)phenyl]thieno[3,2-d]pyrimidin-2-yl]amino]-2-(2-morpholinoethoxy)phenyl]prop-2-enamide,
36: N-[4-methoxy-5-[[4-(1-methylindol-3-yl)thieno[3,2-d]pyrimidin-2-yl]amino]-2-morpholino-phenyl]prop-2-enamide, 37: N-[4-methoxy-5-[[4-[4-(methylamino)phenyl]thieno[3,2-d]pyrimidin-2-yl]amino]-2-morpholino-phenyl]prop-2-enamide,
38: N-[2-(dimethylamino)-4-methoxy-5-[[4-(1-methylindol-3-yl)thieno[3,2-d]pyrimidin-2-yl]amino]phenyl]prop-2-enamide,
39: N-[2-[ethyl(methyl)amino]-4-methoxy-5-[[4-[4-(methylamino)phenyl]thieno[3,2-d]pyrimidin-2-yl]amino]phenyl]prop-2-enamide,
40: N-[2-[ethyl(methyl)amino]-4-methoxy-5-[(4-phenylthieno[2,3-d]pyrimidin-2-yl)amino]phenyl]prop-2-enamide,
41: N-[2-[ethyl(methyl)amino]-4-methoxy-5-[[4-[3-(methylamino)phenyl]thieno[2,3-d]pyrimidin-2-yl]amino]phenyl]prop-2-enamide,
42: N-[4-methoxy-2-(4-methylpiperazin-1-yl)-5-[(4-phenylthieno[2,3-d]pyrimidin-2-yl)amino]phenyl]prop-2-enamide,
43: N-[4-methoxy-5-[[4-[2-(methylamino)phenyl]thieno[2,3-d]pyrimidin-2-yl]amino]-2-(4-methylpiperazin-1-yl)phenyl]prop-2-enamide,
44: N-[4-methoxy-5-[[4-(1-methylindol-7-yl)thieno[3,2-d]pyrimidin-2-yl]amino]-2-(4-methylpiperazin-1-yl)phenyl]prop-2-enamide,
45: N-[5-[[4-(1H-indol-7-yl)thieno[3,2-d]pyrimidin-2-yl]amino]-4-methoxy-2-(4-methylpiperazin-1-yl)phenyl]prop-2-enamide,
46: N-[4-methoxy-2-(4-methylpiperazin-1-yl)-5-[[4-(1-methylpyrrol-3-yl)thieno[2,3-d]pyrimidin-2-yl]amino]phenyl]prop-2-enamide,
47: N-[4-methoxy-2-(4-methylpiperazin-1-yl)-5-[[4-(1H-pyrrol-3-yl)thieno[2,3-d]pyrimidin-2-yl]amino]phenyl]prop-2-enamide,
48: N-[4-methoxy-2-(4-methylpiperazin-1-yl)-5-[[4-(1-methylpyrrol-3-yl)thieno[3,2-d]pyrimidin-2-yl]amino]phenyl]prop-2-enamide,
49: N-[4-methoxy-2-(4-methylpiperazin-1-yl)-5-[[4-(1H-pyrrol-3-yl)thieno[3,2-d]pyrimidin-2-yl]amino]phenyl]prop-2-enamide, and
50: N-[5-[[4-[2-(dimethylamino)phenyl]thieno[2,3-d]pyrimidin-2-yl]amino]-4-methoxy-2-(4-methylpiperazin-1-yl)phenyl]prop-2-enamide,
51: N-[5-[[4-(1H-indol-3-yl)thieno[3,2-d]pyrimidin-2-yl]-methyl-amino]-4-methoxy-2-morpholino-phenyl]prop-2-enamide,
52: N-[4-methoxy-5-[methyl-[4-(1-methylindol-3-yl)thieno[3,2-d]pyrimidin-2-yl]amino]-2-morpholino-phenyl]prop-2-enamide, 53: N-[2-[2-(dimethylamino)ethyl-methyl-amino]-5-[[4-(1H-indol-3-yl)thieno[3,2-d]pyrimidin-2-yl]-methyl-amino]-4-methoxy-phenyl]prop-2-enamide, and
54: N-[2-[2-(dimethylamino)ethyl-methyl-amino]-4-methoxy-5-[methyl-[4-(1-methylindol-3-yl)thieno[3,2-d]pyrimidin-2-yl]amino]phenyl]prop-2-enamide.

17. A pharmaceutical composition comprising an effective amount of a compound of claim 1, or a geometric isomer, enantiomer, diastereomer, racemate, pharmaceutically acceptable salt, prodrugs or solvate thereof, and a pharmaceutically acceptable excipient.

18. A method for inhibiting the growth of a cancer cell which overexpresses Bruton's tyrosine kinase, ITK, JAK3, and epidermal growth factor receptor (EGFR), comprising administering an effective amount of a compound of claim 1 to the cell.

19. A method for inhibiting the growth of a cancer cell according to claim 18, wherein the cancer cell overexpresses BTK.

20. A method for treating a hematological cancer in a subject in need thereof, comprising administering to the subject an effective amount of the pharmaceutical composition of claim 17.

21. The method of claim 20, wherein the hematological cancer is CLL of DLBCL.

22. A method for inhibiting the growth of a cancer cell according to claim 18, wherein the EGFR expressed by the cancer cell is a mutant EGFR.

23. A method for inhibiting the growth of a cancer cell according to claim 22, wherein the a mutant EGFR is a T7090M mutant, an L858R mutant or a delE746-A750 mutant.

24. A method for treating a disease caused by abnormal cell proliferation in a human subject in need thereof comprising administering to the subject an effective amount of the pharmaceutical composition of claim 17.

25. The method according to claim 24, wherein the abnormal cell proliferation is caused by overexpression of EGFR.

26. The method according to claim 25, wherein the abnormal cell proliferation is caused by overexpression of EGFR selected from the group consisting of ErbB1, ErbB32, ErbB3, and ErbB4.

27. The method according to claim 26, wherein the disease is a relapsed or acquired resistant malignant disease.

28. A method for treating NSCLC in a human subject in need thereof comprising administering to the subject an effective amount of the pharmaceutical composition of claim 17.

* * * * *